United States Patent
Law et al.

(10) Patent No.: US 10,449,259 B2
(45) Date of Patent: Oct. 22, 2019

(54) ENZYME-RESPONSIVE PEPTIDE NANOFIBER COMPOSITIONS AND USES THEREOF

(71) Applicant: Cornell University, Ithaca, NY (US)

(72) Inventors: Shek Hang Benedict Law, New York, NY (US); Ching-Hsuan Tung, New York, NY (US); Vanessa Bellat, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/764,188

(22) PCT Filed: Sep. 30, 2016

(86) PCT No.: PCT/US2016/054960
§ 371 (c)(1),
(2) Date: Mar. 28, 2018

(87) PCT Pub. No.: WO2017/059338
PCT Pub. Date: Apr. 6, 2017

(65) Prior Publication Data
US 2018/0296697 A1    Oct. 18, 2018

Related U.S. Application Data

(60) Provisional application No. 62/236,574, filed on Oct. 2, 2015.

(51) Int. Cl.
| | |
|---|---|
| *A61K 47/69* | (2017.01) |
| *A61K 47/42* | (2017.01) |
| *A61K 9/70* | (2006.01) |
| *A61K 47/65* | (2017.01) |
| *A61K 47/60* | (2017.01) |
| *A61P 35/00* | (2006.01) |
| *A61K 38/06* | (2006.01) |
| *A61K 38/20* | (2006.01) |
| *A61K 38/21* | (2006.01) |
| *A61K 38/50* | (2006.01) |
| *A61K 31/167* | (2006.01) |
| *A61K 31/704* | (2006.01) |
| *A61K 9/00* | (2006.01) |
| *A61K 31/5365* | (2006.01) |

(52) U.S. Cl.
CPC ............ *A61K 47/6953* (2017.08); *A61K 9/70* (2013.01); *A61K 31/167* (2013.01); *A61K 31/5365* (2013.01); *A61K 31/704* (2013.01); *A61K 38/063* (2013.01); *A61K 38/2013* (2013.01); *A61K 38/2073* (2013.01); *A61K 38/212* (2013.01); *A61K 38/50* (2013.01); *A61K 47/42* (2013.01); *A61K 47/60* (2017.08); *A61K 47/65* (2017.08); *A61P 35/00* (2018.01); *C12Y 305/01001* (2013.01); *A61K 9/0024* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. |
| 5,580,990 A | 12/1996 | Van Den Berg et al. |
| 5,643,575 A | 7/1997 | Martinez et al. |
| 5,674,534 A | 10/1997 | Zale et al. |
| 5,716,644 A | 2/1998 | Zale et al. |
| 5,985,566 A | 11/1999 | Houthoff et al. |
| 6,133,038 A | 10/2000 | Houthoff et al. |
| 6,468,798 B1 | 10/2002 | Debs et al. |
| 2004/0067503 A1 | 4/2004 | Tan et al. |
| 2014/0066387 A1 | 3/2014 | Gelain et al. |
| 2014/0273148 A1 | 9/2014 | Collier et al. |
| 2014/0302144 A1 | 10/2014 | Koutsopoulos et al. |

FOREIGN PATENT DOCUMENTS

| | | |
|---|---|---|
| WO | WO-96/40073 A2 | 12/1996 |
| WO | WO-99/15154 A1 | 4/1999 |
| WO | WO-00/38651 A1 | 7/2000 |
| WO | WO-2013/155152 A1 | 10/2013 |

OTHER PUBLICATIONS

Alexis, et al., "Factors Affecting the Clearance and Biodistribution of Polymeric Nanoparticles," Molecular Pharmaceutics, 2008, pp. 505-515, vol. 5, No. 4.
Arnida, et al., "Geometry and surface characteristics of gold nanoparticles influence their biodistribution and uptake by macrophages," European Journal of Pharmaceutics and Biopharmaceutics, Apr. 2011, pp. 417-423, vol. 77, Issue 3.
Burns, et al., "Fluorescent Silica Nanoparticles with Efficient Urinary Excretion for Nanomedicine," Nano Letters, 2009, pp. 442-448, vol. 9, No. 1.
Choi, et al., "Renal clearance of quantum dots," Natural Biotechnology, 2007, pp. 1165-1170, vol. 25, No. 10.
Chonn, et al., "Recent advances in liposomal drug-delivery systems," Current Opinion in Biotechnology, 1995, pp. 698-708, vol. 6, Issue 6.
Conda-Sheridan, et al., "Esterase-activated release of naproxen from supramolecular nanofibres," Chemical Communications, Nov. 2014, pp. 13757-13760, vol. 50, Issue 89.

(Continued)

*Primary Examiner* — Marcela M Cordero Garcia
(74) *Attorney, Agent, or Firm* — Foley & Lardner LLP

(57) ABSTRACT

The disclosure provides compositions comprising peptide-based nanofiber precursors and methods of using the same to inhibit cancerous cell growth and/or to deliver therapeutic or diagnostic agents to cells, e.g., cancerous cells. The compositions of the present technology include peptide-based nanofiber precursors as well as carrier complexes comprising a therapeutic or diagnostic agent, and a peptide-based nanofiber precursor. Also provided herein are methods for delivering a therapeutic or diagnostic agent to a cell comprising contacting the cell with a carrier complex including a therapeutic or diagnostic agent, and a peptide-based nanofiber precursor.

19 Claims, 37 Drawing Sheets
Specification includes a Sequence Listing.

(56) References Cited

OTHER PUBLICATIONS

Geng, et al., "Shape effects of filaments versus spherical particles in flow and drug delivery," Nature Nanotechnology, 2007, pp. 249-255, vol. 2.
Gregoriadis, "Engineering liposomes for drug delivery: progress and problems," Trends in Biotechnology, Dec. 1995, pp. 527-537, vol. 13, Issue 12.
International Preliminary Report on Patentability in International Application No. PCT/US2016/US2016/054960 dated Apr. 3, 2018 (10 pages).
International Search Report and Written Opinion in International Application No. PCT/US2016/054960 dated Feb. 1, 2017 (12 pages).
Junttila, et al., "Trastuzumab-DM1 (T-DM1) retains all the mechanisms of action of trastuzumab and efficiently inhibits growth of lapatinib insensitive breast cancer," Breast Cancer Research and Treatment, Jul. 2011, pp. 347-356, vol. 128, Issue 2.
Law, et al., "Protease-sensitive fluorescent nanofibers," Bioconjugate Chemistry, 2007, pp. 1701-1704, vol. 18, No. 6.
Law, et al., "Structural Modification of Protease Inducible Preprogrammed Nanofiber Precursor," Biomacromolecules, Jan. 2008, pp. 421-425, vol. 9, No. 2.
Li, et al., Chirality of Glutathione Surface Coating Affects the Cytotoxicity of Quantum Dots, Angewandte Chemie International Edition, Jun. 20, 2011, pp. 5860-5864, vol. 50, No. 26.
Li, et al., "Pharmacokinetics and Biodistribution of Nanoparticles," Molecular Pharmaceutics, 2008, pp. 496-504, vol. 5, No. 4.
Lichtenberg, et al., "Liposomes: preparation, characterization, and preservation," Methods of Biochemical Analysis, 1988, pp. 337-462, vol. 33.
Mizuguchi, et al., "Intratumor administration of fusogenic liposomes containing fragment A of diphtheria toxin suppresses tumor growth," Cancer Letters, Feb. 1996, pp. 63-69, vol. 100, Issues 1-2.
Phillips, et al., "Targeting HER2-positive breast cancer with trastuzumab-DM1, an antibody-cytotoxic drug conjugate," Cancer Research, Nov. 2008, pp. 9280-9290, vol. 68, No. 22.
Raha, et al., "Peptide-mediated cancer targeting of nanoconjugates," Wires-Nanomedicine and Nanobiotechnology, May-Jun. 2011, pp. 269-281, vol. 3, No. 3.
Reddy, "Controlled-Release, Pegylation, Liposomal Formulations: New Mechanisms in the Delivery of Injectable Drugs", Annals of Pharmacotherapy, Jul. 2000, pp. 915-923, vol. 34, No. 7/8.
Stewart, "[3] Cleavage methods following Boc-based solid-phase peptide synthesis," Methods in Enzymology, 1997, pp. 29-44, vol. 289.
Toft, et al., "Coassembled Cytotoxic and Pegylated Peptide Amphiphiles Form Filamentous Nanostructures with Potent Antitumor Activity in Models of Breast Cancer," ACS Nano, Sep. 2012, pp. 7956-7965, vol. 6, No. 9.
Weiner, "Liposomes for Protein Delivery: Selecting Manufacture and Development Processes," Immunomethods, Jun. 1994, pp. 201-209, vol. 4, Issue 3.
Zha, et al., "Self-assembly of Cytotoxic Peptide Amphiphiles into Supramolecular Membranes for Cancer Therapy," Advanced Healthcare Materials, Jun. 2013, pp. 126-133, vol. 2, No. 1.

FIG. 12A

| Analogues | Peptide Constructs | Ratio | ζ(mV) |
|---|---|---|---|
| NFP | mPEG$_{2000}$- KLDLKLDLKLDLK – Cyanine5.5 | 1 | |
| | mPEG$_{2000}$- KLDLKLDLKLDLC | 39 | |
| GSH-NFP | mPEG$_{2000}$- KLDLKLDLKLDLK – Cyanine5.5 | 1 | -10.1 ± 3.7 |
| | mPEG$_{2000}$- KLDLKLDLKLDLK-GSH | 8 | |
| | mPEG$_{2000}$- KLDLKLDLKLDLC | 31 | |
| K$_2$D$_4$ | mPEG$_{2000}$- KLDLKLDLKLDLK – Cyanine5.5 | 1 | |
| | mPEG$_{2000}$- KKKLDLKLDLKLDLKDDDD | 8 | |
| | mPEG$_{2000}$- KLDLKLDLKLDLC | 31 | |
| 3MA | mPEG$_{2000}$- KLDLKLDLKLDLK – Cyanine5.5 | 1 | |
| | mPEG$_{2000}$- KLDLKLDLKLDLK-3MA | 8 | |
| | mPEG$_{2000}$- KLDLKLDLKLDLC | 31 | |
| MA | mPEG$_{2000}$- KLDLKLDLKLDLK – Cyanine5.5 | 1 | |
| | mPEG$_{2000}$- KLDLKLDLKLDLK-MA | 8 | |
| | mPEG$_{2000}$- KLDLKLDLKLDLC | 31 | |

ENZYME-RESPONSIVE PEPTIDE NANOFIBER COMPOSITIONS AND USES THEREOF

CROSS-REFERENCE TO RELATED APPLICATIONS

This application is the U.S. 371 National Phase Application of PCT/US2016/054960, filed Sep. 30, 2016, which claims the benefit of and priority to U.S. Provisional Application No. 62/236,574 filed Oct. 2, 2015, the content of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Nov. 10, 2016, is named 093873-1126_SL.txt and is 3,432 bytes in size.

GOVERNMENT SUPPORT

This invention was made with Government support under Grant Number TR000457 awarded by the National Institutes of Health. The government has certain rights in the invention.

TECHNICAL FIELD

The present technology relates generally to compositions including peptide-based nanofiber precursors and methods of using the same to inhibit cancerous cell growth and/or to deliver therapeutic or diagnostic agents to cancerous cells.

BACKGROUND

The following description is provided to assist the understanding of the reader. None of the information provided or references cited is admitted to be prior art to the present technology.

Nanomaterials tend to accumulate at tumor sites as a result of leaky vasculature and poor lymphatic drainage. As such, many nanomaterials have been proposed as drug carriers. However, the pharmacokinetic and in vivo distribution of a nanomaterial can be affected by many physicochemical properties (Alexis et al., *Mol Pharm* 5:505-15 (2008)). Smaller nanoparticles (<3-5 nm) are often eliminated from the body by renal clearance and thus have relatively shorter plasma half-lives (Choi et al., *Nat Biotechnol* 25:1165-70 (2007)). On the other hand, larger particles (>10-20 nm) are prompt to be captured by the reticuloendothelial system (Burns et al., *Nano Lett* 9:442-8 (2009)), and therefore, are more likely to be taken up by the liver and spleen (Li & Huang, *Mol Pharm* 5:496-504 (2008)).

Apart from size, the shape of a nanomaterial may impact the pharmacokinetic property and biodistribution of the nanomaterial (Geng et al., *Nat Nanotechnol* 2:249-55 (2007)). For example, after intravenous injection, the uptake of gold nanorods by liver was found to be less than its spherical counterpart of same size (Arnida et al., *Eur J Pharm Biopharm* 77:417-23 (2011)).

SUMMARY

In one aspect, the present disclosure provides a peptide-based nanofiber precursor composition comprising a methoxypolyethylene glycol (mPEG) polymer, a fluorophore and a self-assembling domain comprising the sequence KLDLKLDLKLDLK (SEQ ID NO: 1), wherein the self-assembling domain is interspersed between the fluorophore and the mPEG polymer, wherein each amino acid of SEQ ID NO: 1 is an L-amino acid. In certain embodiments, the peptide-based nanofiber precursor composition further comprises a hexalysine motif (SEQ ID NO: 13), wherein the hexalysine motif (SEQ ID NO: 13) is interspersed between the mPEG polymer and the self-assembling domain. Additionally or alternatively, in some embodiments of the peptide-based nanofiber precursor composition of the present technology, the mPEG polymer is located at the N-terminus. In other embodiments, the mPEG polymer is located at the C-terminus. The mPEG polymer may have a molecular weight from about 1 kDa to about 5 kDa. In some embodiments of the peptide-based nanofiber precursor composition, the mPEG polymer has a molecular weight of about 2 kDa.

Additionally or alternatively, in some embodiments of the peptide-based nanofiber precursor composition, the fluorophore is fluorescein isothiocyanate (FITC), N,N,N',N'-tetramethyl-6-carboxyrhodamine (TAMRA), or Cy5.5® (Thermofisher Scientific, Waltham, Mass.). Other suitable fluorophores include 4-acetamido-4'-isothiocyanatostilbene-2,2'disulfonic acid, acridine and derivatives (acridine, acridine isothiocyanate), Alexa Fluors (Alexa Fluor® 350, Alexa Fluor® 488, Alexa Fluor® 546, Alexa Fluor® 555, Alexa Fluor® 568, Alexa Fluor® 594, Alexa Fluor® 647 (Thermofisher Scientific, Waltham, Mass.)), 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, BODIPY® R-6G (Thermofisher Scientific, Waltham, Mass.), BOPIPY® 530/550 (Thermofisher Scientific, Waltham, Mass.), BODIPY® FL (Thermofisher Scientific, Waltham, Mass.), Brilliant Yellow, Cal Fluor Red 610® (CFR610) (LGC Biosearch Technologies, Petaluma, Calif.), coumarin and derivatives (coumarin, 7-amino-4-methylcoumarin (AMC, Coumarin 120), 7-amino-4-trifluoromethylcouluarin (Coumarin 151)), Cy2® (Thermofisher Scientific, Waltham, Mass.), Cy3® (Thermofisher Scientific, Waltham, Mass.), Cy3.5® (Thermofisher Scientific, Waltham, Mass.), Cy5® (Thermofisher Scientific, Waltham, Mass.), cyanosine, 4',6-diaminidino-2-phenylindole (DAPI), 5', 5"-dibromopyrogallol-sulfonephthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), Eclipse™ (Epoch Biosciences Inc., Sugar Land, Tex.), eosin and derivatives (eosin, eosin isothiocyanate), erythrosin and derivatives (erythrosin B, erythrosin isothiocyanate), ethidium, fluorescein and derivatives (5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, hexachloro-6-carboxyfluorescein (HEX), QFITC (XRITC), tetrachlorofluorescein (TET), fluorescamine, IR144, IR1446, lanthamide phosphors, Malachite Green isothiocyanate, 4-methylumbelliferone, ortho cresolphthalein, nitrotyrosine, pararosaniline, Phenol Red, B-phycoerythrin, R-phycoerythrin, allophycocyanin, o-phthaldialdehyde, Oregon Green® (Thermofisher Scientific, Waltham, Mass.), propidium iodide, pyrene and derivatives (pyrene, pyrene butyrate, succinimidyl 1-pyrene butyrate), QSY® 7 (Thermofisher Scientific, Waltham, Mass.), QSY® 9 (Thermofisher Scientific, Waltham, Mass.), QSY® 21 (Thermofisher Scientific, Waltham, Mass.), QSY® 35 (Thermofisher Scientific, Waltham, Mass.), Reactive Red 4 (Cibacron® Brilliant Red 3B-A, Sigma Aldrich, St. Louis, Mo.), rhodamine and derivatives (6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, sulforhodamine B, sulforhodamine 101, sulfonyl chloride derivative of sulforhodamine 101 (Texas Red), tetramethyl rhodamine, tetramethyl rhodamine isothiocyanate (TRITC), riboflavin, rosolic acid, terbium chelate derivatives, Quasar 670® (LGC Biosearch Technologies, Petaluma, Calif.), and VIC® (Thermofisher Scientific, Waltham, Mass.).

In one aspect, the present disclosure provides a peptide-based nanofiber precursor composition comprising a methoxypolyethylene glycol (mPEG) polymer, Glutathione (GSH) and a self-assembling domain comprising the sequence KLDLKLDLKLDLK (SEQ ID NO: 1), wherein the self-assembling domain is interspersed between GSH and the mPEG polymer, wherein each amino acid of SEQ ID NO: 1 is an L-amino acid. Additionally or alternatively, in some embodiments of the peptide-based nanofiber precursor composition of the present technology, the mPEG polymer is located at the N-terminus or the C-terminus. The mPEG polymer may have a molecular weight from about 1 kDa to about 5 kDa. In some embodiments of the peptide-based nanofiber precursor composition, the mPEG polymer has a molecular weight of about 2 kDa.

In another aspect, the present disclosure provides a peptide-based nanofiber comprising a plurality of peptides, wherein each peptide comprises a methoxypolyethylene glycol (mPEG) polymer, a fluorophore and a self-assembling domain comprising the sequence KLDLKLDLKLDLK (SEQ ID NO: 1), wherein the self-assembling domain is interspersed between the fluorophore and the mPEG polymer, wherein each amino acid of SEQ ID NO: 1 is an L-amino acid. In certain embodiments, each peptide further comprises a hexalysine motif (SEQ ID NO: 13), wherein the hexalysine motif (SEQ ID NO: 13) is interspersed between the mPEG polymer and the self-assembling domain. The mPEG polymer may be located at the N-terminus or the C-terminus of each peptide. The mPEG polymer may have a molecular weight from about 1 kDa to about 5 kDa.

In another aspect, the present disclosure provides a peptide-based nanofiber comprising a plurality of peptides, wherein each peptide comprises a methoxypolyethylene glycol (mPEG) polymer, GSH and a self-assembling domain comprising the sequence KLDLKLDLKLDLK (SEQ ID NO: 1), wherein the self-assembling domain is interspersed between GSH and the mPEG polymer, wherein each amino acid of SEQ ID NO: 1 is an L-amino acid. The mPEG polymer may be located at the N-terminus or the C-terminus of each peptide. The mPEG polymer may have a molecular weight from about 1 kDa to about 5 kDa.

In another aspect, the present disclosure provides a peptide-based nanofiber comprising a mixture of a first plurality of peptides and a second plurality of peptides, wherein each peptide of the first plurality of peptides comprises a first methoxypolyethylene glycol (mPEG) polymer, a first fluorophore, and a first self-assembling domain comprising the sequence KLDLKLDLKLDLK (SEQ ID NO: 1), wherein the first self-assembling domain is interspersed between the first fluorophore and the first mPEG polymer, wherein each amino acid of SEQ ID NO: 1 is an L-amino acid; and wherein each peptide of the second plurality of peptides comprises a second methoxypolyethylene glycol (mPEG) polymer, a second fluorophore, and a second self-assembling domain comprising the sequence KLDLKLDLKLDLK (SEQ ID NO: 1), wherein the second self-assembling domain is interspersed between the second fluorophore and the second mPEG polymer, wherein each amino acid of SEQ ID NO: 1 is an L-amino acid. In certain embodiments of the peptide-based nanofiber, each peptide of the first plurality of peptides comprises a first hexalysine motif (SEQ ID NO: 13), wherein the first hexalysine motif (SEQ ID NO: 13) is interspersed between the first mPEG polymer and the first self-assembling domain. Additionally or alternatively, in some embodiments of the peptide-based nanofiber of the present technology, each peptide of the second plurality of peptides comprises a second hexalysine motif (SEQ ID NO: 13), wherein the second hexalysine motif (SEQ ID NO: 13) is interspersed between the second mPEG polymer and the second self-assembling domain.

In any of the above embodiments, the first mPEG polymer and the second mPEG polymer may have a molecular weight from about 1 kDa to about 5 kDa. The first mPEG polymer and the second mPEG polymer may have the same or different molecular weights. In certain embodiments, the first mPEG polymer and the second mPEG polymer have a molecular weight of about 2 kDa.

In any of the above embodiments of the peptide-based nanofiber, the molar ratio of the first plurality of peptides to the second plurality of peptides is about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:25, 1:30, 1:40, 1:50, 1:60, 1:70, 1:80, 1:90, 1:100, 1:110, 1:120, 1:130, 1:140, 1:150, 1:160, 1:170, 1:180, 1:190, 1:200, or any possible subranges therein. In certain embodiments, the molar ratio of the first plurality of peptides to the second plurality of peptides is 1:1, 1:9, or 1:19. Additionally or alternatively, in some embodiments of the peptide-based nanofiber, the first fluorophore is Cy5.5® (Thermofisher Scientific, Waltham, Mass.). In certain embodiments, the second fluorophore is FITC.

In another aspect, the present disclosure provides a peptide-based nanofiber comprising a mixture of a first plurality of peptides and a second plurality of peptides, wherein each peptide of the first plurality of peptides comprises a first methoxypolyethylene glycol (mPEG) polymer, a first fluorophore, and a first self-assembling domain comprising the sequence KLDLKLDLKLDLK (SEQ ID NO: 1), wherein the first self-assembling domain is interspersed between the first fluorophore and the first mPEG polymer, wherein each amino acid of SEQ ID NO: 1 is an L-amino acid; and wherein each peptide of the second plurality of peptides comprises a second methoxypolyethylene glycol (mPEG) polymer, and a second self-assembling domain comprising the sequence KLDLKLDLKLDLC (SEQ ID NO: 11).

In another aspect, the present disclosure provides a peptide-based nanofiber comprising a mixture of a first plurality of peptides and a second plurality of peptides, wherein each peptide of the first plurality of peptides comprises a first methoxypolyethylene glycol (mPEG) polymer, a first fluorophore, and a first self-assembling domain comprising the sequence KLDLKLDLKLDLK (SEQ ID NO: 1), wherein the first self-assembling domain is interspersed between the first fluorophore and the first mPEG polymer, wherein each amino acid of SEQ ID NO: 1 is an L-amino acid; and wherein each peptide of the second plurality of peptides comprises a second methoxypolyethylene glycol (mPEG) polymer, GSH and a second self-assembling domain comprising the sequence KLDLKLDLKLDLK (SEQ ID NO: 1).

The first mPEG polymer and the second mPEG polymer may have a molecular weight from about 1 kDa to about 5 kDa. The first mPEG polymer and the second mPEG polymer may have the same or different molecular weights. In certain embodiments, the first mPEG polymer and the second mPEG polymer have a molecular weight of about 2 kDa.

In any of the above embodiments of the peptide-based nanofiber, the molar ratio of the first plurality of peptides to the second plurality of peptides is about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:25, 1:30, 1:39, 1:40, 1:50, or any possible subranges therein. In certain embodiments, the molar ratio of the first plurality of peptides to the second plurality of peptides is 1:1, 1:9, or 1:39. In any of the above embodiments of the peptide-based nanofiber, the molar ratio of the first plurality of peptides to the second plurality of peptides is about 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 40:1, 50:1, or any possible subranges therein. Additionally or alternatively, in some embodiments of the peptide-based nanofiber, the first fluorophore is Cy5.5® (Thermofisher Scientific, Waltham, Mass.).

In another aspect, the present disclosure provides a peptide-based nanofiber comprising a mixture of a first plurality of peptides, a second plurality of peptides, and a third plurality of peptides, wherein each peptide of the first plurality of peptides comprises a first methoxypolyethylene glycol (mPEG) polymer, a first fluorophore, and a first self-assembling domain comprising the sequence KLDLKLDLKLDLK (SEQ ID NO: 1), wherein the first self-assembling domain is interspersed between the first fluorophore and the first mPEG polymer, wherein each amino acid of SEQ ID NO: 1 is an L-amino acid; wherein each peptide of the second plurality of peptides comprises a second methoxypolyethylene glycol (mPEG) polymer, and a second self-assembling domain comprising the sequence KLDLKLDLKLDLC (SEQ ID NO: 11); and wherein each peptide of the third plurality of peptides comprises a third methoxypolyethylene glycol (mPEG) polymer, GSH and a third self-assembling domain comprising the sequence KLDLKLDLKLDLK (SEQ ID NO: 1). In some embodiments, the molar ratio of the third plurality of peptides to the first and second plurality of peptides is about 1:49, 2:48, 3:47, 4:46, 5:45, 6:44, 7:43, 8:42, 9:41, 10:40, or any possible subrange therein. In certain embodiments, the molar ratio of the first plurality of peptides to the second plurality of peptides to the third plurality of peptide is 1:31:8, 1:32:7, 1:33:6, 1:34:5, 1:35:4, 1:36:3, 1:37:2, 1:38:1, 1:38.1:0.9, 1:31.2:0.8, or any possible subrange therein.

In any of the above embodiments, the peptide-based nanofibers of the present technology have lengths between about 50 nm to about 400 nm. In certain embodiments, the peptide-based nanofibers have a length of about 100 nm.

The peptide-based nanofiber precursor compositions or the peptide-based nanofibers of the present technology may be surface functionalized with one or more targeting ligands selected from the group consisting of antibodies, polymers, and peptide moieties. Suitable peptide moieties include, but are not limited to, Bombesin (BBN), Somatostatin, Allatostatin 1, Follicle-stimulating hormone analog FSH-33, LyP-1 peptide, Fibroblast growth factor analogs, Hepatocarcinoma targeting peptide, Peptide GFE, Epidermal Growth Factor, cetuximab, RGD tripeptide, CendR peptide, peptide F3, α-MSH peptide, Enterotoxin (STh), cyclic decapeptide CGLIIQKNEC (SEQ ID NO: 6), WIFPWIQL (SEQ ID NO: 7) peptide, CREKA (SEQ ID NO: 8) peptide, IPLVVPL (SEQ ID NO: 9) peptide, KTLLPTP (SEQ ID NO: 10) peptide, and antitumor-antibody-derived peptides.

In another aspect, the present disclosure provides a carrier complex comprising a therapeutic or diagnostic agent conjugated to any of the peptide-based nanofibers described herein. The carrier complexes disclosed herein may comprise nanofibers having lengths between about 50 nm to about 400 nm.

The carrier complexes of the present technology may include one or more therapeutic agents selected from the group consisting of 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, *Bacillus* calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxil, aldoxorubicin, doxifluridine, edrecolomab, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, ibritumomab tiuxetan, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mertansine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, trastuzumab emtansine, tretinoin, trimitrexate, alrubicin, vincristine, vinblastine, vindestine, vinorelbine, vorinostat, and zoledronic acid.

Additionally or alternatively, the carrier complexes disclosed herein may include one or more diagnostic agents, such as a nanoparticle, a radioactive substance, a dye, a fluorescent compound, a contrast agent, a bioluminescent compound, an enzyme, or an enhancing agent.

In one aspect, the present technology provides methods for delivering a therapeutic or diagnostic agent to a cancerous cell comprising contacting the cell with any of the carrier complexes described herein.

In another aspect, the present technology provides methods for delivering a therapeutic or diagnostic agent to a cancerous cell in a subject in need thereof comprising administering to the subject an effective amount of any of the carrier complexes disclosed herein. In some embodiments, the subject is diagnosed with breast cancer, brain cancer, ovarian cancer, or prostate cancer.

In another aspect, the present disclosure provides methods for inhibiting cancerous cell growth in a subject in need thereof, comprising administering to the subject a therapeutically effective amount of the peptide-based nanofiber precursor compositions or the peptide-based nanofibers of the present technology. In some embodiments of the methods, the subject is diagnosed with breast cancer, ovarian cancer, brain cancer, or prostate cancer. In certain embodiments, the breast cancer is HER2-positive breast cancer or triple-negative breast cancer. In some embodiments, the subject is human.

In some embodiments of the methods, the peptide-based nanofiber precursor compositions or the peptide-based nanofibers of the present technology are administered orally, topically, intranasally, systemically, locally intramuscularly, intravenously, subcutaneously, intracerebroventricularly, intrathecally, intratumorally, transdermally or with iontophoresis. Administration of the peptide-based nanofiber precursor compositions or the peptide-based nanofibers may result in a reduction in the number of tumors in the subject and/or a decrease in the severity of tumors in the subject.

Additionally or alternatively, in certain embodiments of the methods, the peptide-based nanofiber precursor compositions or the peptide-based nanofibers of the present technology are administered at regular intervals over a period of one, two or several months. In some embodiments, the regular intervals are every day, every other day, every 3 days, every 4 days, every 5 days, every 6 days or once a week.

BRIEF DESCRIPTION OF THE DRAWINGS

FIG. 2B displays HPLC spectra of the assembled FITC-NFP1 and FITC-NFP2 nanofibers (50 μM of the peptide content) before and 24 hours after CathB activation (0.3 U) in sodium acetate buffer (50 μM, pH 4) at room temperature. All samples were dissociated with DMSO prior to analysis with HPLC. FIG. 2B shows that FITC-NFP1 was cleaved into multiple fragments after CathB digestion, whereas only one fragment was identified for FITC-NFP2 post CathB treatment. FIG. 2C shows transmission electron microscopy (TEM) images (80,000× magnification) for FITC-NFP1 (10 μM) and FITC-NFP2 (10 μM) nanofibers before and after CathB digestion. The samples were stained with uranyl formate (0.5% v/v) prior to TEM analysis. FIG. 2C shows that FITC-NFP1 nanofibers were degraded and became shorter in length after CathB digestion. Conversely, FITC-NFP2 nanofibers aggregated to form an interfibril network after incubation with CathB.

FIG. 3A shows the schematic representation of fluorescent nanofibers, FITC-NFP1 and FITC-NFP2, assembled from a comixture of Cy5.5-conjugated and FITC-conjugated peptide constructs to study their cellular uptake. The FITC-conjugated peptide served as the spacer to adjust the distance between Cy5.5 to minimize the self-quenching effect. FIG. 3B shows a schematic representation that demonstrates how CathB digestion induced the transformation and, thus, changes in the fluorescence of the quenched Cy5.5-NFP1 and Cy5.5-NFP2. CathB digestion of quenched NFP1 could be monitored by the recovery of the fluorescence signal. Only a minimal fluorescence change was observed in quenched NFP2 upon CathB activation. FIG. 3C compares the fluorescence intensities of NFP1 and NFP2 formulations (0.1 μM of peptide content) containing different ratios of Cy5.5 and FITC fluorophores in PBS buffer. FIG. 3D compares the fluorescence intensities of Cy5.5-NFP1 and Cy5.5-NFP2 nanofibers (0.1 μM of peptide content) before and 24 hours after CathB activation (0.3 U) in sodium acetate buffer (50 μM, pH 4) at room temperature.

FIG. 4A shows the cellular distributions of the fluorescent Cy5.5-FITC-NFP1 and Cy5.5-FITC-NFP2. MDA-MB-468 cell images were acquired 6 hours after incubation with the NFP1 or NFP2 nanofibers (10 μM of peptide content). DAPI and LysoTracker were used for staining nuclei and lysosomes respectively. Both fluorescent nanofibers were internalized within the lysosomes (see white arrows). FIG. 4B shows a comparison of the intracellular degradation of the quenched Cy5.5-NFP1 and Cy5.5-NFP2 according to the recovery of the fluorescent signals. Cell images were acquired 6 hours and 24 hours after incubation with the nanofibers. Quenched Cy5.5-NFP1 degraded rapidly over time (see white arrow), whereas no degradation was observed with quenched Cy5.5-NFP2. All images were adjusted to the same window setting.

FIG. 5A shows the synthetic schemes of the DM1-conjugated peptide constructs. FIG. 5B displays MALDI-TOF spectra confirming the synthesis of all the peptide constructs and their intermediates.

FIG. 6A displays HPLC spectra of the nanofibers (50 μM) before and after incubation with CathB (0.3 U) in sodium acetate buffer (50 μM; pH 4) for 24 hours at room temperature. All samples were dissociated with DMSO prior to injection into the HPLC. FIG. 6B displays MALDI-TOF spectra of the identified drug metabolites collected from the HPLC fractions. Lys-MCC-DM1 and Leu-Lys-MCC-DM1 had two isoforms.

FIG. 7A shows the cell viability of naked NFP1 and NFP2 (10 nM to 10 µM) in human HER2-positive breast cancer (BT474) and triple-negative breast cancer (MDA-MB-231 and MDA-MB-468) cell lines. FIG. 7B shows the cell viability of DM1-MCC-NFP1, DM1-MCC-NFP2, T-DM1, and DM1 (100 pM to 50 µM) in human HER2-positive breast cancer (BT474) and triple-negative breast cancer (MDA-MB-231 and MDA-MB-468) cell lines. All the experiments were performed in triplicate. Data were presented as mean±standard deviation (SD) (*, P<0.05).

FIG. 12A shows the amino acid sequence of the peptide constructs used for assembling the different nanofiber precursor analogues (SEQ ID NOS 1, 11, 1, 1, 11, 1, 12, 11, 1, 1, 11, 1, 1 and 11, respectively, in order of appearance).

DETAILED DESCRIPTION

Figure 1:
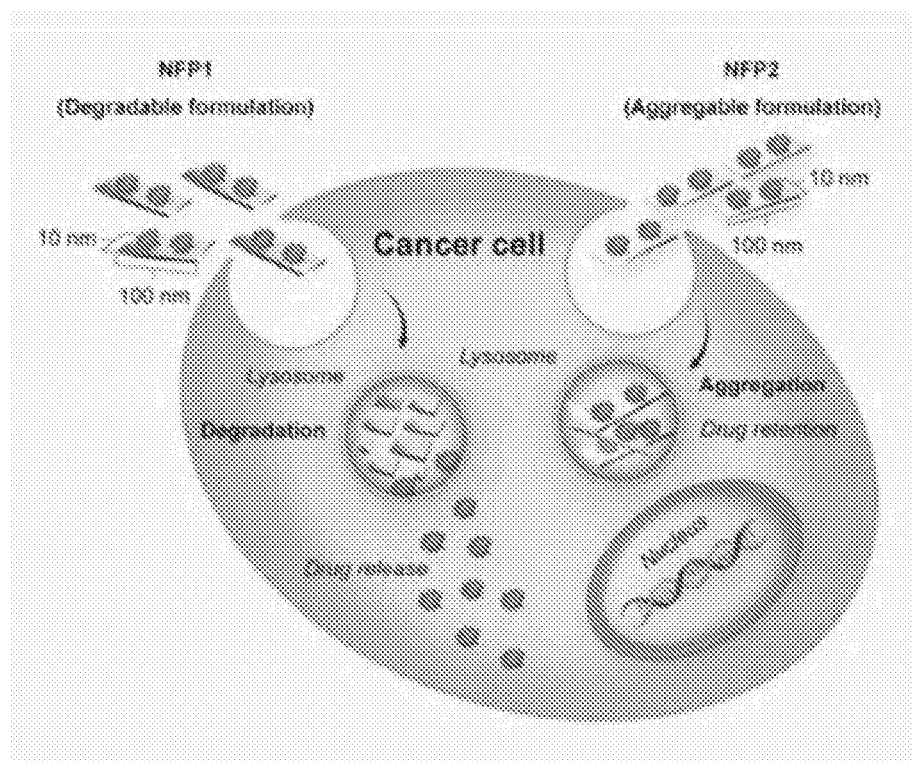
FIG. 1 shows two peptide-based nanofiber precursor compositions (NFP1 and NFP2) that can function as drug carriers. NFP1 and NFP2 form nanofibers that internalize into cancer cells via endocytosis. Digestion of NFP1 by lysosomal cathepsin B (CathB) leads to rapid cytoplasmic release of the drug payload. In contrast, NFP2 nanofibers formed large aggregates within the lysosomes, thereby contributing to the controlled payload release property.

It is to be appreciated that certain aspects, modes, embodiments, variations and features of the present technology are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which the present technology belongs.

All numerical designations, e.g., pH, temperature, time, concentration and molecular weight, including ranges, are approximations which are varied (+) or (−) by increments of 1.0 or 0.1, as appropriate, or alternatively by a variation of +/−10%, or alternatively 5% or alternatively 2%. Unless indicated otherwise, it is to be understood, although not always explicitly stated, that all numerical designations are preceded by the term "about".

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, peptide-based nanofiber precursor composition, or peptide-based nanofiber to a subject includes any route of introducing or delivering to a subject a compound to perform its intended function. Administration can be carried out by any suitable route, including orally, intranasally, parenterally (intravenously, intramuscularly, intraperitoneally, or subcutaneously), intratumorally, or topically. Administration includes self-administration and the administration by another.

As used herein, the term "amino acid" includes naturally-occurring amino acids and synthetic amino acids, as well as amino acid analogs that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acids can be referred to herein by either their commonly known three letter symbols or by the one-letter symbols recommended by the IUPAC-IUB Biochemical Nomenclature Commission.

As used herein, "carrier complex" means the association of at least one therapeutic or diagnostic agent with at least one peptide-based nanofiber of the present technology. The therapeutic or diagnostic agent and peptide-based nanofiber can associate by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

As used herein, a "control" is an alternative sample used in an experiment for comparison purposes. A control can be "positive" or "negative". For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in partial or full amelioration of one or more symptoms of breast, ovarian, brain, or prostate cancer. In the context of therapeutic or prophylactic applications, in some embodiments, the amount of a composition administered to the subject will depend on the type and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. For example, a "therapeutically effective amount" of the peptide-based nanofiber precursor compositions, peptide-based nanofibers, or carrier complexes of the present technology includes levels at which a the presence, frequency, or severity of one or more signs, symptoms, or risk factors of breast cancer, ovarian cancer, brain cancer, or prostate cancer are reduced or eliminated.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

As used herein, "triple negative breast cancer" or "TNBC" refer to any breast cancer wherein the cancerous cells do not express the estrogen receptor (ER), progesterone receptor (PR) and HER2.

As used herein, "prevention" or "preventing" of a disease or condition refers to a compound that, in a statistical sample, reduces the occurrence of the disease or medical condition in the treated sample relative to an untreated control sample, or delays the onset of one or more symptoms of the disorder or condition relative to the untreated control sample.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, the term "subject" or "patient" includes both human and veterinary subjects, for example, humans, non-human primates, dogs, cats, sheep, mice, horses, and cows.

As used herein, the terms "treating" or "treatment" or "alleviation" or "amelioration" refers to the treatment of a disease or medical condition, in a subject, such as a human, and includes: (i) inhibiting a disease or medical condition, i.e., arresting its development; (ii) relieving a disease or medical condition, i.e., causing regression of the disease or medical condition; (iii) slowing progression of the disease or medical condition; and/or (iv) inhibiting, relieving, or slowing progression of one or more symptoms of the disease or medical condition.

Peptide-Based Nanofiber Precursor Compositions

The present disclosure provides peptide-based nanofiber precursor compositions, and peptide-based nanofibers that can biomechanically remodel upon enzyme activation (e.g., CathB cleavage) to create either a degradable or an aggregable effect, within the lysosomal compartment of a cell. See FIG. 1. The peptide-based nanofiber precursor compositions of the present technology can self-assemble into single-layer nanofiber structures in aqueous media. See, e.g., Law et al., *Biomacromolecules*, 9:421-425 (2008).

In some embodiments, the peptide-based nanofiber precursor compositions of the present technology comprise a methoxypolyethylene glycol (mPEG) polymer, a fluorophore and a self-assembling domain comprising the sequence KLDLKLDLKLDLK (SEQ ID NO: 1) (FIG. 2). The self-assembling domain (a) is composed of L-amino acids, and (b) is interspersed between the fluorophore and the mPEG polymer. In certain embodiments of the peptide-based nanofiber precursor compositions, each individual peptide further comprises a hexalysine motif (SEQ ID NO: 13), wherein the hexalysine motif (SEQ ID NO: 13) is interspersed between the mPEG polymer and the self-assembling domain.

In some embodiments, the peptide-based nanofiber precursor compositions of the present technology comprise a methoxypolyethylene glycol (mPEG) polymer, an antioxidant, and a self-assembling domain comprising the sequence KLDLKLDLKLDLK (SEQ ID NO: 1), wherein the self-assembling domain is interspersed between the antioxidant and the mPEG polymer, wherein each amino acid of SEQ ID NO: 1 is an L-amino acid and the antioxidant is GSH, Mercaptosuccinic acid, or 3-mercaptopropionic acid.

Additionally or alternatively, in any of the above embodiments of the peptide-based nanofiber precursor compositions of the present technology, the mPEG polymer is located at the N-terminus or at the C-terminus. The mPEG polymer may have a molecular weight from about 1 kDa to about 5 kDa. In some embodiments of the peptide-based nanofiber precursor compositions, the mPEG polymer has a molecular weight of about 1 kDa, 1.5 kDa, 2 kDa, 2.5 kDa, 3 kDa, 3.5 kDa, 4 kDa, 4.5 kDa or 5 kDa.

Additionally or alternatively, in any of the above embodiments of the peptide-based nanofiber precursor compositions, the fluorophore is fluorescein isothiocyanate (FITC), N,N,N',N'-tetramethyl-6-carboxyrhodamine (TAMRA), or Cy5.5® (Thermofisher Scientific, Waltham, Mass.). Other suitable fluorophores include 4-acetamido-4'-isothiocyanatostilbene-2,2'disulfonic acid, acridine and derivatives (acridine, acridine isothiocyanate), Alexa Fluors (Alexa Fluor® 350, Alexa Fluor® 488, Alexa Fluor® 546, Alexa Fluor® 555, Alexa Fluor® 568, Alexa Fluor® 594, Alexa Fluor® 647 (Thermofisher Scientific, Waltham, Mass.)), 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, BODIPY® R-6G (Thermofisher Scientific, Waltham, Mass.), BOPIPY® 530/550 (Thermofisher Scientific, Waltham, Mass.), BODIPY® FL (Thermofisher Scientific, Waltham, Mass.), Brilliant Yellow, Cal Fluor Red 610® (CFR610) (LGC Biosearch Technologies, Petaluma, Calif.), coumarin and derivatives (coumarin, 7-amino-4-methylcoumarin (AMC, Coumarin 120), 7-amino-4-trifluoromethylcouluarin (Coumarin 151)), Cy2® (Thermofisher Scientific, Waltham, Mass.), Cy3® (Thermofisher Scientific, Waltham, Mass.), Cy3.5® (Thermofisher Scientific, Waltham, Mass.), Cy5® (Thermofisher Scientific, Waltham, Mass.), cyanosine, 4',6-diaminidino-2-phenylindole (DAPI), 5', 5"-dibromopyrogallol-sulfonephthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), Eclipse™ (Epoch Biosciences Inc., Sugar Land, Tex.), eosin and derivatives (eosin, eosin isothiocyanate), erythrosin and derivatives (erythrosin B, erythrosin isothiocyanate), ethidium, fluorescein and derivatives (5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, hexachloro-6-carboxyfluorescein (HEX), QFITC (XRITC), tetrachlorofluorescein (TET), fluorescamine, IR144, IR1446, lanthamide phosphors, Malachite Green isothiocyanate, 4-methylumbelliferone, ortho cresolphthalein, nitrotyrosine, pararosaniline, Phenol Red, B-phycoerythrin, R-phycoerythrin, allophycocyanin, o-phthaldialdehyde, Oregon Green® (Thermofisher Scientific, Waltham, Mass.), propidium iodide, pyrene and derivatives (pyrene, pyrene butyrate, succinimidyl 1-pyrene butyrate), QSY® 7 (Thermofisher Scientific, Waltham, Mass.), QSY® 9 (Thermofisher Scientific, Waltham, Mass.), QSY® 21 (Thermofisher Scientific, Waltham, Mass.), QSY® 35 (Thermofisher Scientific, Waltham, Mass.), Reactive Red 4 (Cibacron® Brilliant Red 3B-A, Sigma Aldrich, St. Louis, Mo.), rhodamine and derivatives (6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, sulforhodamine B, sulforhodamine 101, sulfonyl chloride derivative of sulforhodamine 101 (Texas Red), tetramethyl rhodamine, tetramethyl rhodamine isothiocyanate (TRITC), riboflavin, rosolic acid, terbium chelate derivatives, Quasar 670® (LGC Biosearch Technologies, Petaluma, Calif.), and VIC® (Thermofisher Scientific, Waltham, Mass.).

In some embodiments, the peptide-based nanofibers of the present technology comprise a plurality of peptides, wherein each peptide comprises a methoxypolyethylene glycol (mPEG) polymer, a fluorophore and a self-assembling domain comprising the sequence KLDLKLDLKLDLK (SEQ ID NO: 1), wherein the self-assembling domain is interspersed between the fluorophore and the mPEG polymer, wherein each amino acid of SEQ ID NO: 1 is an L-amino acid. In certain embodiments, each peptide further comprises a hexalysine motif (SEQ ID NO: 13), wherein the hexalysine motif (SEQ ID NO: 13) is interspersed between the mPEG polymer and the self-assembling domain.

In other embodiments, the peptide-based nanofibers of the present technology comprise a plurality of peptides, wherein each peptide comprises a methoxypolyethylene glycol (mPEG) polymer, an antioxidant (e.g., GSH, mercaptosuccinic acid, or 3-mercaptopropionic acid) and a self-assembling domain comprising the sequence KLDLKLDLKLDLK (SEQ ID NO: 1), wherein the self-assembling domain is interspersed between the antioxidant and the mPEG polymer, wherein each amino acid of SEQ ID NO: 1 is an L-amino acid.

In any of the above embodiments of the peptide-based nanofibers, the mPEG polymer may be located at the N-terminus or the C-terminus of each peptide. The mPEG polymer may have a molecular weight from about 1 kDa to about 5 kDa.

In some embodiments, the peptide-based nanofibers of the present technology comprise a mixture of a first plurality of peptides and a second plurality of peptides, wherein each peptide of the first plurality of peptides comprises a first methoxypolyethylene glycol (mPEG) polymer, a first fluorophore, and a first self-assembling domain comprising the sequence KLDLKLDLKLDLK (SEQ ID NO: 1), wherein the first self-assembling domain is interspersed between the first fluorophore and the first mPEG polymer, wherein each amino acid of SEQ ID NO: 1 is an L-amino acid; and wherein each peptide of the second plurality of peptides comprises a second methoxypolyethylene glycol (mPEG) polymer, a second fluorophore, and a second self-assembling domain comprising the sequence KLDLKLD-LKLDLK (SEQ ID NO: 1), wherein the second self-assembling domain is interspersed between the second fluorophore and the second mPEG polymer, wherein each amino acid of SEQ ID NO: 1 is an L-amino acid. In certain embodiments of the peptide-based nanofiber, each peptide of the first plurality of peptides comprises a first hexalysine motif (SEQ ID NO: 13), wherein the first hexalysine motif (SEQ ID NO: 13) is interspersed between the first mPEG polymer and the first self-assembling domain. Additionally or alternatively, in some embodiments of the peptide-based nanofiber of the present technology, each peptide of the second plurality of peptides comprises a second hexalysine motif (SEQ ID NO: 13), wherein the second hexalysine motif (SEQ ID NO: 13) is interspersed between the second mPEG polymer and the second self-assembling domain. In some embodiments of the peptide-based nanofiber, the molar ratio of the first plurality of peptides to the second plurality of peptides is about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:25, 1:30, 1:40, 1:50, 1:60, 1:70, 1:80, 1:90, 1:100, 1:110, 1:120, 1:130, 1:140, 1:150, 1:160, 1:170, 1:180, 1:190, 1:200, or any possible subranges therein. In certain embodiments, the molar ratio of the first plurality of peptides to the second plurality of peptides is 1:1, 1:9, or 1:19. Additionally or alternatively, in some embodiments of the peptide-based nanofiber, the first fluorophore is Cy5.5® (Thermofisher Scientific, Waltham, Mass.). In certain embodiments, the second fluorophore is FITC.

In some embodiments, the peptide-based nanofibers of the present technology comprise a mixture of a first plurality of peptides and a second plurality of peptides, wherein each peptide of the first plurality of peptides comprises a first methoxypolyethylene glycol (mPEG) polymer, a first fluorophore, and a first self-assembling domain comprising the sequence KLDLKLDLKLDLK (SEQ ID NO: 1), wherein the first self-assembling domain is interspersed between the first fluorophore and the first mPEG polymer, wherein each amino acid of SEQ ID NO: 1 is an L-amino acid; and wherein each peptide of the second plurality of peptides comprises a second methoxypolyethylene glycol (mPEG) polymer, and a second self-assembling domain comprising the sequence KLDLKLDLKLDLC (SEQ ID NO: 11).

In some embodiments, the peptide-based nanofibers of the present technology comprise a mixture of a first plurality of peptides and a second plurality of peptides, wherein each peptide of the first plurality of peptides comprises a first methoxypolyethylene glycol (mPEG) polymer, a first fluorophore, and a first self-assembling domain comprising the sequence KLDLKLDLKLDLK (SEQ ID NO: 1), wherein the first self-assembling domain is interspersed between the first fluorophore and the first mPEG polymer, wherein each amino acid of SEQ ID NO: 1 is an L-amino acid; and wherein each peptide of the second plurality of peptides comprises a second methoxypolyethylene glycol (mPEG) polymer, an antioxidant, and a second self-assembling domain comprising the sequence KLDLKLDLKLDLK (SEQ ID NO: 1), wherein the antioxidant is GSH, mercaptosuccinic acid, or 3-mercaptopropionic acid.

In any of the above embodiments of the peptide-based nanofibers, the molar ratio of the first plurality of peptides to the second plurality of peptides is about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:25, 1:30, 1:40, 1:50, or any possible subranges therein. In certain embodiments, the molar ratio of the first plurality of peptides to the second plurality of peptides is 1:1, 1:9, or 1:39. In any of the above embodiments of the peptide-based nanofiber, the molar ratio of the first plurality of peptides to the second plurality of peptides is about 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 40:1, 45:1, 49:1, 50:1, or any possible subranges therein. Additionally or alternatively, in some embodiments of the peptide-based nanofiber, the first fluorophore is any fluorophore disclosed herein (e.g., Cy5.5® (Thermofisher Scientific, Waltham, Mass.)).

In some embodiments, the peptide-based nanofibers of the present technology comprise a mixture of a first plurality of peptides, a second plurality of peptides, and a third plurality of peptides, wherein each peptide of the first plurality of peptides comprises a first methoxypolyethylene glycol (mPEG) polymer, a first fluorophore, and a first self-assembling domain comprising the sequence KLDLKLD-LKLDLK (SEQ ID NO: 1), wherein the first self-assembling domain is interspersed between the first fluorophore and the first mPEG polymer, wherein each amino acid of SEQ ID NO: 1 is an L-amino acid; wherein each peptide of the second plurality of peptides comprises a second methoxypolyethylene glycol (mPEG) polymer, and a second self-assembling domain comprising the sequence KLDLKLD-LKLDLC (SEQ ID NO: 11); and wherein each peptide of the third plurality of peptides comprises a third methoxypolyethylene glycol (mPEG) polymer, a third self-assembling domain comprising the sequence KLDLKLD-LKLDLK (SEQ ID NO: 1) and an antioxidant, wherein the antioxidant is GSH, mercaptosuccinic acid, or 3-mercaptopropionic acid. In some embodiments, the molar ratio of the third plurality of peptides to the first and second plurality of peptides is about 1:49, 2:48, 3:47, 4:46, 5:45, 6:44, 7:43, 8:42, 9:41, 10:40, or any possible subrange therein. In certain embodiments, the molar ratio of the first plurality of peptides to the second plurality of peptides to the third plurality of peptide is 1:31:8, 1:32:7, 1:33:6, 1:34:5, 1:35:4, 1:36:3, 1:37:2, 1:38:1, 1:38.1:0.9, or 1:31.2:0.8.

In some embodiments, the peptide-based nanofibers of the present technology comprise a mixture of a first plurality of peptides, a second plurality of peptides, and a third plurality of peptides, wherein each peptide of the first plurality of peptides comprises a first methoxypolyethylene glycol (mPEG) polymer, a first fluorophore, and a first self-assembling domain comprising the sequence KLDLKLD-LKLDLK (SEQ ID NO: 1), wherein the first self-assembling domain is interspersed between the first fluorophore and the first mPEG polymer, wherein each amino acid of SEQ ID NO: 1 is an L-amino acid; wherein each peptide of the second plurality of peptides comprises a second methoxypolyethylene glycol (mPEG) polymer, and a second self-assembling domain comprising the sequence KLDLKLD-LKLDLC (SEQ ID NO: 11); and wherein each peptide of the third plurality of peptides comprises a third methoxypolyethylene glycol (mPEG) polymer and a third self-assembling domain comprising the sequence KKKLD-LKLDLKLDLKDDDD (SEQ ID NO: 12). In some embodiments, the molar ratio of the third plurality of peptides to the first and second plurality of peptides is about 1:49, 2:48, 3:47, 4:46, 5:45, 6:44, 7:43, 8:42, 9:41, 10:40, or any possible subrange therein. In certain embodiments, the molar ratio of the first plurality of peptides to the second plurality of peptides to the third plurality of peptide is 1:31:8, 1:32:7, 1:33:6, 1:34:5, 1:35:4, 1:36:3, 1:37:2, 1:38:1, 1:38.1:0.9, or 1:31.2:0.8.

Additionally or alternatively, in some embodiments of the peptide-based nanofibers disclosed herein, the first mPEG polymer, the second mPEG polymer, or the third PEG polymer may be located at the N-terminus of each individual peptide. In other embodiments, the first mPEG polymer, the second mPEG polymer, or the third PEG polymer is located at the C-terminus of each individual peptide.

The first mPEG polymer, the second mPEG polymer, and the third mPEG polymer (if present) may have a molecular weight from about 1 kDa to about 5 kDa. The first mPEG polymer, the second mPEG polymer, and the third mPEG polymer (if present) may have the same or different molecular weights. In some embodiments of the peptide-based nanofibers of the present technology, the first mPEG polymer, the second mPEG polymer, and the third mPEG polymer (if present) have molecular weights of about 1 kDa, 1.5 kDa, 2 kDa, 2.5 kDa, 3 kDa, 3.5 kDa, 4 kDa, 4.5 kDa or 5 kDa. In certain embodiments, the first mPEG polymer, the second mPEG polymer, and the third mPEG polymer (if present) have a molecular weight of about 2 kDa.

In any of the above embodiments, the peptide-based nanofibers of the present technology have lengths between about 50 nm to about 400 nm. In certain embodiments, the peptide-based nanofibers of the present technology have lengths of about 50 nm, 60 nm, 70 nm, 80 nm, 90 nm, 100 nm, 125 nm, 150 nm, 175 nm, 200 nm, 225 nm, 250 nm, 275 nm, 300 nm, 325 nm, 350 nm, 375 nm, or 400 nm.

The peptide-based nanofiber precursor compositions or peptide-based nanofibers of the present technology exhibit differential responses towards CathB, a proteolytic enzyme commonly upregulated in cancer cells. In some embodiments, the peptide-based nanofiber precursor compositions or peptide-based nanofibers are degraded by CathB. In certain embodiments, CathB treatment induces the peptide-based nanofibers to aggregate and form an interfibril network. In particular, the aggregable properties of the peptide-based nanofibers of the present technology were surprising because the hydrophilic mPEG polymer is expected to prevent aggregation after self-assembly into nanofibers.

In some embodiments, the peptide-based nanofiber precursor compositions or peptide-based nanofibers of the present technology have a high drug loading capacity and exhibit an antibody-like intracellular degradation mechanism. The peptide-based nanofibers displayed a unique single-layered structure with a high aspect ratio (0.5×5×100 nm$^3$) that resulted in increased uptake by tumors (FIGS. 12-16) compared to other nanofiber compositions known in the art. See Conda-Sheridan et al., *Chem. Commun.* 50(89): 13757-60 (2014); Zha et al., *Adv. Healthcare Mater.* 2(1): 126-33 (2013); Toft et al., *ACS Nano* 6(9):7956-65 (2012). While not wishing to be bound by theory, the increased uptake of the peptide-based nanofibers of the present technology may reflect enhanced permeability and retention of these compositions by tumors. The peptide-based nanofibers of the present technology can infiltrate the tumor tissue and in some embodiments, can transform into larger interfibril networks to minimize lymphatic clearance, upon exposure to tumor-associated proteases such as cathepsin B. Accordingly, the peptide-based nanofibers of the present technology may provide a controlled release environment when employed as a drug carrier, and may also prolong the drug-tumor exposure period, thereby increasing treatment efficacy.

The peptide-based nanofiber precursor compositions or peptide-based nanofibers of the present technology may be surface functionalized with one or more targeting ligands selected from the group consisting of antibodies, polymers, and peptide moieties. Suitable peptide moieties include, but are not limited to, Bombesin (BBN), Somatostatin, Allatostatin 1, Follicle-stimulating hormone analog FSH-33, LyP-1 peptide, Fibroblast growth factor analogs, Hepatocarcinoma targeting peptide, peptide GFE, Epidermal Growth Factor, cetuximab, RGD tripeptide, CendR peptide, peptide F3, α-MSH peptide, Enterotoxin (STh), cyclic decapeptide CGLIIQKNEC (SEQ ID NO: 6), WIFPWIQL (SEQ ID NO: 7) peptide, CREKA (SEQ ID NO: 8) peptide, IPLVVPL (SEQ ID NO: 9) peptide, KTLLPTP (SEQ ID NO: 10) peptide, and antitumor-antibody-derived peptides.

In some embodiments, the peptide-based nanofiber precursor compositions or peptide-based nanofibers of the present technology may be surface functionalized with HER2 antibodies, Estrogen Receptor antibodies, Progesterone Receptor antibodies, B7-H3-specific mAb 376.96, VEGF antibodies, folate receptor alpha antibodies, Trop2 antibodies, Delta-like ligand 4 (DLL4) antibodies, NKG2A receptor antibodies, EGFR antibodies, and/or PSA antibodies.

Peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.*, 289, Academic Press, Inc., New York (1997). Antibodies, polymers, and peptide moieties may be surface functionalized to the peptide-based nanofiber precursor compositions or peptide-based nanofibers of the present technology using any suitable methods known in the art (Raha et al., *Wires-Nanomed Nanobiotechnol*, 3(3):269-281 (2011)).

Therapeutic Agents

Chemotherapeutic agents that may be used in accordance with the embodiments described herein are often cytotoxic in nature and may include, but are not limited to, alkylating agents, antimetabolites, anti-tumor antibiotics, topoisomerase inhibitors, mitotic inhibitors hormone therapy, targeted therapeutics and immunotherapeutics. In some embodiments, the chemotherapeutic agents that may be used as therapeutic agents in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, *Bacillus* calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxil, aldoxorubicin, doxifluridine, edrecolomab, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte—colony stimulating factor, granulocyte macrophage-colony stimulating factor, hexamethylmelamine, hydrocortisone hydroxyurea, ibritumomab, ibritumomab tiuxetan, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mertansine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, trastuzumab emtansine, tretinoin, trimitrexate, alrubicin, vincristine, vinblastine, vindestine, vinorelbine, vorinostat, or zoledronic acid.

Therapeutic antibodies and functional fragments thereof, that may be used as therapeutic agents in accordance with the embodiments of the disclosure include, but are not limited to, alemtuzumab, bevacizumab, cetuximab, edrecolomab, gemtuzumab, ibritumomab tiuxetan, panitumumab, rituximab, tositumomab, trastuzumab, trastuzumab emtansine and other antibodies associated with specific diseases listed herein.

Radioisotopes that may be used as therapeutic agents in accordance with the embodiments of the disclosure include, but are not limited to, $^{32}$P, $^{89}$Sr, $^{90}$Y, $^{99m}$Tc, $^{99}$Mo, $^{131}$I, $^{153}$Sm, $^{177}$Lu, $^{186}$Re, $^{213}$Bi, $^{223}$Ra and $^{225}$Ac.

Diagnostic Agents

The peptide-based nanofibers described herein may associate with, or may be conjugated to one or more diagnostic agents (or "imaging agents"), forming a diagnostic-peptide nanofiber conjugate.

The diagnostic-peptide nanofiber conjugate may be useful to target and visualize cancerous cells in vivo via an imaging method (e.g., positron emission tomography (PET), computer assisted tomography (CAT), single photon emission computerized tomography, x-ray, fluoroscopy, and magnetic resonance imaging (MRI)). As such, the diagnostic-peptide nanofiber conjugate may be used in methods for diagnosing, and/or monitoring diseases such as breast cancer, brain cancer, ovarian cancer, or prostate cancer. Accordingly, in one aspect, the present disclosure provides methods for delivering a diagnostic agent (e.g., imaging agent) to a cancerous cell comprising contacting the cell with a carrier complex comprising a peptide-based nanofiber and a diagnostic agent.

In some embodiments, a diagnostic agent may include, but is not limited to a fluorescent, luminescent, or magnetic protein, peptide or derivatives thereof (e.g., genetically engineered variants). Fluorescent proteins that may be used include, but are not limited to, green fluorescent protein (GFP), enhanced GFP (EGFP), red, blue, yellow, cyan, and sapphire fluorescent proteins, and reef coral fluorescent protein. Luminescent proteins that may be used include, but are not limited to, luciferase, aequorin and derivatives thereof. Numerous fluorescent and luminescent dyes and proteins are known in the art (see, e.g., U.S. Patent Application Publication 2004/0067503; Valeur, B., "Molecular Fluorescence: Principles and Applications," John Wiley and Sons, 2002; Handbook of Fluorescent Probes and Research Products, Molecular Probes, 9th edition, 2002; and The Handbook-A Guide to Fluorescent Probes and Labeling Technologies, Invitrogen, 10th edition, available at the Invitrogen web site; both of which are hereby incorporated by reference as if fully set forth herein).

Additionally or alternatively, in some embodiments, a peptide-based nanofiber may be conjugated to or otherwise associated with a non-protein diagnostic agent such as a nanoparticle, radioactive substances (e.g., radioisotopes, radionuclides, radiolabels or radiotracers), dyes, contrast agents, fluorescent compounds or molecules, bioluminescent compounds or molecules, enzymes and enhancing agents (e.g., paramagnetic ions). In addition, it should be noted that some nanoparticles, for example quantum dots and metal nanoparticles may also be suitable for use as a diagnostic agent and a therapeutic agent (e.g., using hyperthermal and photodynamic therapies as well as diagnostic agents through fluorescence and/or MRI contrast).

Fluorescent and luminescent substances that may be used as an additional diagnostic agent in accordance with the embodiments of the disclosure include, but are not limited to, a variety of organic or inorganic small molecules commonly referred to as "dyes," "labels," or "indicators." Suitable fluorescent substances include, but are not limited to the following fluorophores: 4-acetamido-4'-isothiocyanatostilbene-2,2' disulfonic acid, acridine and derivatives (acridine, acridine isothiocyanate), Alexa Fluors (Alexa Fluor® 350, Alexa Fluor® 488, Alexa Fluor® 546, Alexa Fluor® 555, Alexa Fluor® 568, Alexa Fluor® 594, Alexa Fluor® 647 (Thermofisher Scientific, Waltham, Mass.)), 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, BODIPY® R-6G (Thermofisher Scientific, Waltham, Mass.), BOPIPY® 530/550 (Thermofisher Scientific, Waltham, Mass.), BODIPY® FL (Thermofisher Scientific, Waltham, Mass.), Brilliant Yellow, Cal Fluor Red 610® (CFR610) (LGC Biosearch Technologies, Petaluma, Calif.), coumarin and derivatives (coumarin, 7-amino-4-methylcoumarin (AMC, Coumarin 120), 7-amino-4-trifluoromethylcouluarin (Coumarin 151)), Cy2® (Thermofisher Scientific, Waltham, Mass.), Cy3® (Thermofisher Scientific, Waltham, Mass.), Cy3.5® (Thermofisher Scientific, Waltham, Mass.), Cy5® (Thermofisher Scientific, Waltham, Mass.), cyanosine, 4',6-diaminidino-2-phenylindole (DAPI), 5', 5"-dibromopyrogallol-sulfonephthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), Eclipse™ (Epoch Biosciences Inc., Sugar Land, Tex.), eosin and derivatives (eosin, eosin isothiocyanate), erythrosin and derivatives (erythrosin B, erythrosin isothiocyanate), ethidium, fluorescein and derivatives (5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, hexachloro-6-carboxyfluorescein (HEX), QFITC (XRITC), tetrachlorofluorescein (TET), fluorescamine, IR144, IR1446, lanthamide phosphors, Malachite Green isothiocyanate, 4-methylumbelliferone, ortho cresolphthalein, nitrotyrosine, pararosaniline, Phenol Red, B-phycoerythrin, R-phycoerythrin, allophycocyanin, o-phthaldialdehyde, Oregon Green® (Thermofisher Scientific, Waltham, Mass.), propidium iodide, pyrene and derivatives (pyrene, pyrene butyrate, succinimidyl 1-pyrene butyrate), QSY® 7 (Thermofisher Scientific, Waltham, Mass.), QSY® 9 (Thermofisher Scientific, Waltham, Mass.), QSY® 21 (Thermofisher Scientific, Waltham, Mass.), QSY® 35 (Thermofisher Scientific, Waltham, Mass.), Reactive Red 4 (Cibacron® Brilliant Red 3B-A, Sigma Aldrich, St. Louis, Mo.), rhodamine and derivatives (6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, sulforhodamine B, sulforhodamine 101, sulfonyl chloride derivative of sulforhodamine 101 (Texas Red), tetramethyl rhodamine, tetramethyl rhodamine isothiocyanate (TRITC), riboflavin, rosolic acid, terbium chelate derivatives, Quasar 670® (LGC Biosearch Technologies, Petaluma, Calif.), and VIC® (Thermofisher Scientific, Waltham, Mass.).

Enzymes that may be used as a diagnostic agent in accordance with the embodiments of the disclosure include, but are not limited to, horseradish peroxidase, alkaline phosphatase, acid phosphatase, glucose oxidase, β-galactosidase, β-glucoronidase or β-lactamase. Such enzymes may be used in combination with a chromogen, a fluorogenic compound or a luminogenic compound to generate a detectable signal.

Radioactive substances that may be used as a diagnostic agent in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, and $^{225}$Ac.

Paramagnetic ions that may be used as a diagnostic agent in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

When the diagnostic agent is a radioactive metal or paramagnetic ion, the agent may be reacted with another long-tailed reagent having a long tail with one or more chelating groups attached to the long tail for binding these ions. The long tail may be a polymer such as a polylysine, polysaccharide, or other derivatized or derivatizable chain having pendant groups to which may be added for binding to the metals or ions. Examples of chelating groups that may be used according to the disclosure include, but are not limited to, ethylenediaminetetraacetic acid (EDTA), diethylenetriaminepentaacetic acid (DTPA), DOTA, NOTA, NETA, porphyrins, polyamines, crown ethers, bis-thiosemicarbazones, polyoximes, and like groups. The chelate may be linked to an antibody or functional antibody fragment by a group which enables the formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with antibodies that specifically target select cancerous cells or tissues. Macrocyclic chelates such as NOTA, DOTA, and TETA can be used with a variety of metals and radiometals including, but not limited to, radionuclides of gallium, yttrium and copper, respectively. Other ring-type chelates such as macrocyclic polyethers, which are of interest for stably binding nuclides, such as $^{223}$Ra for RAIT may be used. In certain embodiments, chelating moieties may be used to attach a PET diagnostic agent, such as an Al-$^{18}$F complex, to a targeting molecule for use in PET analysis.

Carrier Complexes

At least one diagnostic or therapeutic agent as described above, and at least one peptide-based nanofiber as described above, associate to form a carrier complex. The diagnostic or therapeutic agent and peptide-based nanofiber can associate by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

The type of association between the diagnostic or therapeutic agents and peptide-based nanofibers typically depends on, for example, functional groups available on the diagnostic or therapeutic agent and functional groups available on the peptide-based nanofiber.

For a chemical bond or physical bond, a functional group on the diagnostic or therapeutic agent typically associates with a functional group on the peptide-based nanofiber. Alternatively, a functional group on the peptide-based nanofiber associates with a functional group on the diagnostic or therapeutic agent.

The functional groups on the diagnostic or therapeutic agent and peptide-based nanofiber can associate directly. For example, a functional group (e.g., a sulfhydryl group) on a diagnostic or therapeutic agent can associate with a functional group (e.g., sulfhydryl group) on a peptide-based nanofiber to form a disulfide.

Alternatively, the functional groups can associate through a cross-linking agent (i.e., linker). Some examples of cross-linking agents are described below. The cross-linker can be attached to either the diagnostic or therapeutic agent or the peptide-based nanofiber.

The linker may or may not affect the number of net charges of the peptide-based nanofiber. Typically, the linker will not contribute to the net charge of the peptide-based nanofiber.

The number of diagnostic or therapeutic agents, or peptide-based nanofibers in the carrier complex is limited by the capacity of the peptide-based nanofiber precursor to accommodate multiple diagnostic or therapeutic agents or the capacity of the diagnostic or therapeutic agent to accommodate multiple peptide-based nanofibers. For example, steric hindrance may hinder the capacity of the peptide-based nanofiber to accommodate especially large diagnostic or therapeutic agents.

The number of diagnostic or therapeutic agents or peptide-based nanofibers in the carrier complex is also limited by the number of functional groups present on the other. For example, the maximum number of diagnostic or therapeutic agents associated with a peptide-based nanofiber depends on the number of functional groups present on the peptide-based nanofiber. Alternatively, the maximum number of peptide-based nanofibers associated with a diagnostic or therapeutic agent depends on the number of functional groups present on the diagnostic or therapeutic agent.

In one embodiment, the carrier complex comprises at least one diagnostic or therapeutic agent, or at least two diagnostic or therapeutic agents, associated with a peptide-based nanofiber. A peptide-based nanofiber containing several (e.g., 3, 4, 5 or more) functional groups can be associated with several (e.g., 3, 4, 5 or more) diagnostic or therapeutic agents.

In another embodiment, the carrier complex comprises at least one peptide-based nanofiber, and preferably at least two peptide-based nanofibers, associated with a diagnostic or therapeutic agent. For example, a diagnostic or therapeutic agent containing several functional groups (e.g., 3, 4, 5 or more) can be associated with several (e.g., 3, 4, or 5 or more) peptide-based nanofibers.

In yet another embodiment, the carrier complex comprises one peptide-based nanofiber associated to one diagnostic or therapeutic agent.

In one embodiment, a carrier complex comprises at least one diagnostic or therapeutic agent chemically bonded (e.g., conjugated) to at least one peptide-based nanofiber. The diagnostic or therapeutic agent can be chemically bonded to a peptide-based nanofiber by any method known to those in the art.

For example, a functional group on the diagnostic or therapeutic agent may be directly attached to a functional group on the peptide-based nanofiber. Some examples of suitable functional groups include, for example, amino, carboxyl, sulfhydryl, maleimide, isocyanate, isothiocyanate and hydroxyl.

The diagnostic or therapeutic agent may also be chemically bonded to the peptide-based nanofiber by means of cross-linking agents, such as dialdehydes, carbodiimides, dimaleimides, and the like. Cross-linking agents can, for example, be obtained from Pierce Biotechnology, Inc. (Rockford, Ill.). Additional cross-linking agent include the platinum cross-linking agents described in U.S. Pat. Nos. 5,580,990; 5,985,566; and 6,133,038 of Kreatech Biotechnology, B.V., Amsterdam, The Netherlands.

The functional group on the diagnostic or therapeutic agent may be different from the functional group on the peptide-based nanofiber. Alternatively, the functional group on the diagnostic or therapeutic agent and peptide-based nanofiber can be the same. Homobifunctional cross-linkers are typically used to cross-link identical functional groups. Examples of homobifunctional cross-linkers include EGS (i.e., ethylene glycol bis[succinimidylsuccinate]), DSS (i.e., disuccinimidyl suberate), DMA (i.e., dimethyl adipimidate.2 HCl), DTSSP (i.e., 3,3'-dithiobis[sulfosuccinimidylpropionate])), DPDPB (i.e., 1,4-di-[3'-(2'-pyridyldithio)-propionamido]butane), and BMH (i.e., bis-maleimidohexane). Such homobifunctional cross-linkers are also available from Pierce Biotechnology, Inc.

To chemically bond the diagnostic or therapeutic agents and the peptide-based nanofibers, the diagnostic or therapeutic agents, peptide-based nanofibers, and cross-linker are typically mixed together. The order of addition of the diagnostic or therapeutic agents, peptide-based nanofibers, and cross-linker is not important. For example, the peptide-based nanofiber can be mixed with the cross-linker, followed by addition of the diagnostic or therapeutic agent. Alternatively, the diagnostic or therapeutic agent can be mixed with the cross-linker, followed by addition of the peptide-based nanofiber. Alternatively, the diagnostic or therapeutic agents and the peptide-based nanofibers are mixed, followed by addition of the cross-linker.

The chemically bonded carrier complexes deliver the diagnostic or therapeutic agents to a cell. In some embodiments, the diagnostic or therapeutic agent functions in the cell without being cleaved from the peptide-based nanofiber.

In other instances, it may be beneficial to cleave the diagnostic or therapeutic agent from the peptide-based nanofiber. The web-site of Pierce Biotechnology, Inc. described above can also provide assistance to one skilled in the art in choosing suitable cross-linkers which can be cleaved by, for example, enzymes in the cell. Thus the diagnostic or therapeutic agent can be separated from the peptide-based nanofiber. Examples of cleavable linkers include SMPT (i.e., 4-succinimidyloxycarbonyl-methyl-a-[2-pyridyldithio]toluene), Sulfo-LC-SPDP (i.e., sulfosuccinimidyl 6-(3-[2-pyridyldithio]-propionamido)hexanoate), LC-SPDP (i.e., succinimidyl 6-(3-[2-pyridyldithio]-propionamido)hexanoate), Sulfo-LC-SPDP (i.e. sulfosuccinimidyl 6-(3-[2-pyridyldithio]-propionamido)hexanoate), SPDP (i.e., N-succinimidyl 3-[2-pyridyldithio]-propionamidohexanoate), and AEDP (i.e., 3-[(2-aminoethyl)dithio]propionic acid.HCl).

In another embodiment, a carrier complex comprises at least one diagnostic or therapeutic agent physically bonded with at least one peptide-based nanofiber. Any method known to those in the art can be employed to physically bond the diagnostic or therapeutic agents with the peptide-based nanofibers. For example, the peptide-based nanofibers and diagnostic or therapeutic agents can be placed in a container and agitated, by for example, shaking the container, to mix the peptide-based nanofibers and diagnostic or therapeutic agents.

The peptide-based nanofibers can be modified by any method known to those in the art. For instance, the peptide-based nanofiber may be modified by means of cross-linking agents or functional groups, as described above. The linker may or may not affect the number of net charges of the peptide-based nanofiber. In certain embodiments, the linker will not contribute to the net charge of the peptide-based nanofiber. In some embodiments, the peptide-based nanofiber may be modified by incorporating a pH-sensitive linker, such as a hydrazone group, so that a therapeutic or diagnostic agent could be effectively released within the lysosome and tumor acidic environment. Other exemplary cleavable linkers include linkers that are responsive to tumor-associated enzymes (including proteases, esterases, hydrolases) as well as external stimuli such as light, temperature, magnetic field etc.

Therapeutic Methods

The following discussion is presented by way of example only, and is not intended to be limiting.

One aspect of the present technology includes methods of treating breast cancer, brain cancer, ovarian cancer, or prostate cancer in a subject diagnosed as having, suspected as having, or at risk of having breast cancer, brain cancer, ovarian cancer, or prostate cancer. In certain embodiments, the breast cancer is HER2-positive breast cancer or triple-negative breast cancer. In therapeutic applications, compositions or medicaments comprising a peptide-based nanofiber precursor composition, peptide-based nanofiber, or carrier complex of the present technology, are administered to a subject suspected of, or already suffering from such a disease, such as, e.g., breast cancer, ovarian cancer, brain cancer, or prostate cancer, in an amount sufficient to cure, or at least partially arrest, the symptoms of the disease, including its complications and intermediate pathological phenotypes in development of the disease.

Subjects suffering from breast cancer, ovarian cancer, brain cancer, or prostate cancer can be identified by any or a combination of diagnostic or prognostic assays known in the art. For example, typical symptoms of breast cancer, ovarian cancer, brain cancer, or prostate cancer include, but are not limited to, tumor growth, bloating, abdominal distention or discomfort, bladder or rectum pressure, constipation, vaginal bleeding, indigestion and acid reflux, shortness of breath, tiredness, weight loss, early satiety, pelvic and abdominal pain, nausea and vomiting, diarrhea, changes in breast size or shape, skin dimpling, nipple inversion or skin change, nipple abnormalities, single-duct blood-stained discharge, axillary lumps, urinary frequency, urinary urgency, decreased urine stream, hematuria, bone pain, uremia, lower extremity pain, and edema.

In some embodiments, subjects treated with the peptide-based nanofiber precursor composition, peptide-based nanofiber, or carrier complex of the present technology will show amelioration or elimination of one or more of the following symptoms of breast cancer, brain cancer, ovarian cancer, or prostate cancer: tumor growth, bloating, abdominal distention or discomfort, bladder or rectum pressure, constipation, vaginal bleeding, indigestion and acid reflux, shortness of breath, tiredness, weight loss, early satiety, pelvic and abdominal pain, nausea and vomiting, diarrhea, changes in breast size or shape, skin dimpling, nipple inversion or skin change, nipple abnormalities, single-duct blood-stained discharge, axillary lumps, urinary frequency, urinary urgency, decreased urine stream, hematuria, bone pain, uremia, lower extremity pain, and edema.

Prophylactic Methods

In one aspect, the present technology provides a method for preventing or delaying the onset of breast cancer, ovarian cancer, brain cancer, or prostate cancer, or symptoms of breast cancer, ovarian cancer, brain cancer, or prostate cancer in a subject at risk of having breast cancer, ovarian cancer, brain cancer, or prostate cancer.

Subjects at risk for breast cancer, ovarian cancer, brain cancer, or prostate cancer can be identified by, e.g., any or a combination of diagnostic or prognostic assays known in the art. In prophylactic applications, pharmaceutical compositions or medicaments of peptide-based nanofiber precursor compositions, peptide-based nanofibers, or carrier complexes of the present technology, are administered to a subject susceptible to, or otherwise at risk of a disease or condition such as e.g., breast cancer, ovarian cancer, brain cancer, or prostate cancer, in an amount sufficient to eliminate or reduce the risk, or delay the outset of the disease, including biochemical, histologic and/or behavioral symptoms of the disease, its complications and intermediate pathological phenotypes presenting during development of the disease. Administration of a prophylactic peptide-based nanofiber precursor composition, peptide-based nanofiber, or carrier complex of the present technology can occur prior to the manifestation of symptoms characteristic of the disease or disorder, such that the disease or disorder is prevented or, alternatively, delayed in its onset.

In some embodiments, treatment with the peptide-based nanofiber precursor composition, peptide-based nanofiber, or carrier complex of the present technology will prevent or delay the onset of one or more of the following symptoms of breast cancer, ovarian cancer, brain cancer, or prostate cancer: tumor growth, bloating, abdominal distention or discomfort, bladder or rectum pressure, constipation, vaginal bleeding, indigestion and acid reflux, shortness of breath, tiredness, weight loss, early satiety, pelvic and abdominal pain, nausea and vomiting, diarrhea, changes in breast size or shape, skin dimpling, nipple inversion or skin change, nipple abnormalities, single-duct blood-stained discharge, axillary lumps, urinary frequency, urinary urgency, decreased urine stream, hematuria, bone pain, uremia, lower extremity pain, and edema.

For therapeutic and/or prophylactic applications, a peptide-based nanofiber precursor composition, peptide-based nanofiber, or carrier complex of the present technology is administered to the subject. In some embodiments, the peptide-based nanofiber precursor composition, peptide-based nanofiber, or carrier complex of the present technology is administered one, two, three, four, or five times per day. In some embodiments, the peptide-based nanofiber precursor composition, peptide-based nanofiber, or carrier complex of the present technology is administered more than five times per day. Additionally or alternatively, in some embodiments, the peptide-based nanofiber precursor composition, peptide-based nanofiber, or carrier complex of the present technology is administered every day, every other day, every third day, every fourth day, every fifth day, or every sixth day. In some embodiments, the peptide-based nanofiber precursor composition, peptide-based nanofiber, or carrier complex of the present technology is administered weekly, bi-weekly, tri-weekly, or monthly. In some embodiments, the peptide-based nanofiber precursor composition, peptide-based nanofiber, or carrier complex of the present technology is administered for a period of one, two, three, four, or five weeks. In some embodiments, the peptide-based nanofiber precursor composition, peptide-based nanofiber, or carrier complex of the present technology is administered for six weeks or more. In some embodiments, the peptide-based nanofiber precursor composition, peptide-based nanofiber, or carrier complex of the present technology is administered for twelve weeks or more. In some embodiments, the peptide-based nanofiber precursor composition, peptide-based nanofiber, or carrier complex of the present technology is administered for a period of less than one year. In some embodiments, the peptide-based nanofiber precursor composition, peptide-based nanofiber, or carrier complex of the present technology is administered for a period of more than one year.

Modes of Administration and Effective Dosages

The peptide-based nanofiber precursor compositions or peptide-based nanofibers of the present technology, or carrier complexes including the same, useful in the methods of the present technology may be administered to a subject in an amount effective in treating or preventing breast, brain, ovarian, or prostate cancers. The effective amount is determined during pre-clinical trials and clinical trials by methods familiar to physicians and clinicians.

An effective amount of a peptide-based nanofiber precursor composition, peptide-based nanofiber, or a carrier complex disclosed herein useful in the methods of the present technology, for example in a pharmaceutical composition, may be administered to a subject in need thereof by any of a number of well-known methods for administering pharmaceutical compounds.

The peptide-based nanofiber precursor composition, peptide-based nanofiber, or a carrier complex including the same may be administered systemically or locally. In one embodiment, the peptide-based nanofiber precursor composition, peptide-based nanofiber, or carrier complex is administered intravenously. For example, the peptide-based nanofiber precursor compositions, peptide-based nanofibers, or carrier complexes useful in the methods of the present technology may be administered via rapid intravenous bolus injection. In some embodiments, the peptide-based nanofiber precursor composition, peptide-based nanofiber, or carrier complex is administered as a constant rate intravenous infusion.

The peptide-based nanofiber precursor composition, peptide-based nanofiber, or carrier complex may also be administered orally, topically, intranasally, intramuscularly, subcutaneously, intratumorally or transdermally. In one particular embodiment, transdermal administration of the peptide-based nanofiber precursor composition, peptide-based nanofiber, or carrier complex is by iontophoresis, which permits delivery across the skin by an electric current.

Other routes of administration include intracerebroventricularly or intrathecally. Intracerebroventiculatly refers to administration into the ventricular system of the brain. Intrathecally refers to administration into the space under the arachnoid membrane of the spinal cord.

The peptide-based nanofiber precursor compositions, peptide-based nanofibers, or carrier complexes useful in the methods of the present technology may also be administered to mammals by sustained release, as is known in the art. Sustained release administration is a method of drug delivery to achieve a certain level of the drug over a particular period of time. The level typically is measured by serum or plasma concentration.

Any formulation known in the art of pharmacy is suitable for administration of the peptide-based nanofiber precursor compositions, peptide-based nanofibers, or carrier complexes useful in the methods of the present technology. For oral administration, liquid or solid formulations may be used. Some examples of formulations include tablets, gelatin capsules, pills, troches, elixirs, suspensions, syrups, wafers, chewing gum and the like. The peptide-based nanofiber precursor compositions, peptide-based nanofibers, or carrier complexes can be mixed with a suitable pharmaceutical vehicle or excipient as understood by practitioners in the art. Examples of vehicles and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the peptide-based nanofiber precursor compositions, peptide-based nanofibers, or carrier complexes useful in the methods of the present technology may utilize conventional diluents, carriers, or excipients etc., such as those known in the art, can be employed to deliver the peptide-based nanofiber precursor compositions, peptide-based nanofibers, or carrier complexes of the present technology. For example, the formulations may comprise one or more of the following: a stabilizer, a surfactant, such as a nonionic surfactant, and optionally a salt and/or a buffering agent. The peptide-based nanofiber precursor compositions, peptide-based nanofibers, or carrier complexes may be delivered in the form of an aqueous solution, or in a lyophilized form.

In some embodiments, the stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. In some embodiments, the stabilizer or combination of stabilizers constitutes from about 0.1% to about 10% weight for weight of the formulated composition.

In some embodiments, the surfactant is a nonionic surfactant (such as a polysorbate), an anionic surfactant (such as dioctyl sodium sulfosuccinate), a cationic surfactant (such as cetylpyridinium chloride), or a combination thereof. Examples of suitable non-ionic surfactants include polyoxyethylene sorbitan esters (e.g., Tween-20 and Tween-80), p-t-octyl phenol polyoxyethylenes (e.g., Triton X-45, Triton X-100, Triton X-114, and Triton X-305), a polyethylene glycol or a polyoxyethylene polyoxypropylene glycol, such as Pluronic F-68, nonylphenoxypoloxyethylenes (e.g., Igepal CO series), and polyoxyethylene ethers (e.g. Brij 36T, Brij 52, Brij 56, Brij 76, Brij 96, Texaphor A6, Texaphor A14, and Texaphor A60), at from about 0.001% (w/v) to about 10% (w/v).

The salt or buffering agent may be any salt or buffering agent, such as for example, sodium chloride, or sodium/potassium phosphate, respectively. In certain embodiments, the buffering agent maintains the pH of the pharmaceutical composition in the range of about 5.5 to about 7.5. The salt and/or buffering agent is also useful to maintain the osmolality at a level suitable for administration to a human or an animal. In some embodiments, the salt or buffering agent is present at a roughly isotonic concentration of about 150 mM to about 300 mM.

The formulations of the peptide-based nanofiber precursor compositions, peptide-based nanofibers, or carrier complexes useful in the methods of the present technology may additionally contain one or more conventional additives. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

In some embodiments, compositions including the peptide-based nanofiber precursor compositions, peptide-based nanofibers, or carrier complexes of the present technology may include one or more of salicylates such as, e.g., sodium salicylate, 3-methoxysalicylate, 5-methoxysalicylate and homovanilate; cholesterol derivatives such as bile acids, e.g., taurocholic, taurodeoxycholic, deoxycholic, cholic, glycholic, lithocholate, chenodeoxycholic, ursodeoxycholic, ursocholic, dehydrocholic, and fusidic acid; cetyl pyridinium chloride; acylcarnitines, acylcholines and acyl amino acids such as lauroylcarnitine, myristoylcarnitine, palmitoylcarnitine, lauroylcholine, myristoylcholine, palmitoylcholine, hexadecyllysine, N-acylphenylalanine, N-acylglycine; phospholipids such as lysolecithin, lysophosphatidylethanolamine, diheptanoylphosphatidylcholine and dioctylphosphatidylcholine; ethylene-diaminetetraacetic acid; alkyl saccharides such as lauryl maltoside, lauroyl sucrose, myristoyl sucrose, and palmitoyl sucrose; fatty acid derivatives of PEG such as Labrasol, Labrafac; and mixtures of mono-, di- and triglycerides containing medium-chain-length fatty acids (caprylic, capric and lauric acids).

The mammal can be any mammal, including, for example, farm animals, such as sheep, pigs, cows, and horses; pet animals, such as dogs and cats; laboratory animals, such as rats, mice and rabbits. In one embodiment, the mammal is a human.

The peptide-based nanofiber precursor compositions, peptide-based nanofibers, or carrier complexes of the present technology may include a vehicle, which can be a solvent or dispersion medium containing, for example, water, ethanol, polyol (for example, glycerol, propylene glycol, and liquid polyethylene glycol, and the like), or suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included in the composition to prevent oxidation. In many cases, it is desirable to include isotonic agents, for example, sugars, polyalcohols such as mannitol, sorbitol, or sodium chloride. Prolonged absorption of the injectable compositions can be brought about by including in the composition an agent which delays absorption, for example, aluminum monostearate or gelatin.

Sterile injectable solutions can be prepared by incorporating the active compound (e.g., the peptide-based nanofiber precursor compositions, peptide-based nanofibers, or carrier complexes of the present technology) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use, such as a mouthwash. Pharmaceutically compatible binding agents, and/or adjuvant materials may be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the peptide-based nanofiber precursor compositions, peptide-based nanofibers, or carrier complexes of the present technology can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of the peptide-based nanofiber precursor compositions, peptide-based nanofibers, or carrier complexes of the present technology as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

Peptide-based nanofiber precursor compositions, peptide-based nanofibers or carrier complexes of the present technology can be formulated in a carrier system. The carrier can be a colloidal system. The colloidal system can be a liposome, a phospholipid bilayer vehicle. In one embodiment, the peptide-based nanofiber precursor compositions, peptide-based nanofibers or carrier complexes of the present technology are encapsulated in a liposome while maintaining structural integrity. As one skilled in the art will appreciate, there are a variety of methods to prepare liposomes. (See Lichtenberg, et al., *Methods Biochem. Anal.* 33:337-462 (1988); Anselem, et al., *Liposome Technology*, CRC Press (1993)). Liposomal formulations can delay clearance and increase cellular uptake (See Reddy, *Ann. Pharmacother.* 34 (78):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the peptide-based nanofiber precursor compositions, peptide-based nanofibers, or carrier complexes of the present technology can be embedded in the polymer matrix, while maintaining structural integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.* 34:915-923 (2000). A polymer formulation for human growth hormone (hGH) has been used in clinical trials. (See Kozarich and Rich, *Chemical Biology* 2:548-552 (1998).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the peptide-based nanofiber precursor compositions, peptide-based nanofibers, or carrier complexes of the present technology are prepared with carriers that will protect the peptide-based nanofiber precursor compositions, peptide-based nanofibers, or carrier complexes of the present technology against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Such formulations can be prepared using known techniques. The materials can also be obtained commercially, e.g., from Alza Corporation (Mountain View, Calif., USA) and Nova Pharmaceuticals, Inc. (Sydney, AU). Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The peptide-based nanofiber precursor compositions, peptide-based nanofibers, or carrier complexes of the present technology can also be formulated to enhance intracellular delivery. For example, liposomal delivery systems are known in the art. See, e.g., Chonn and Cullis, *Curr. Opin. Biotech.* 6:698-708 (1995); Weiner, *Immunometh.* 4(3): 201-9 (1994); Gregoriadis, *Trends Biotechnol.* 13(12):527-37 (1995). Mizguchi, et al., *Cancer Lett.* 100:63-69 (1996), describes the use of fusogenic liposomes to deliver a protein to cells both in vivo and in vitro Dosage, toxicity and therapeutic efficacy of the peptide-based nanofiber precursor compositions, peptide-based nanofibers, or carrier complexes of the present technology can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, the peptide-based nanofiber precursor compositions, peptide-based nanofibers, or carrier complexes of the present technology exhibit high therapeutic indices. While the peptide-based nanofiber precursor compositions, peptide-based nanofibers, or carrier complexes of the present technology that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any peptide-based nanofiber precursor composition, peptide-based nanofiber, or carrier complex of the present technology used in the methods described herein, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the peptide-based nanofiber precursor compositions, peptide-based nanofibers, or carrier complexes of the present technology, sufficient for achieving a therapeutic or prophylactic effect, ranges from about 0.000001 mg per kilogram body weight per day to about 10,000 mg per kilogram body weight per day. In some embodiments, the dosage ranges will be from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of the peptide-based nanofiber precursor compositions, peptide-based nanofibers, or carrier complexes of the present technology ranges from 0.1-10,000 micrograms per kg body weight. In one embodiment, peptide-based nanofiber precursor composition, peptide-based nanofiber, or carrier complex concentrations in a carrier range from 0.2 to 2000 micrograms per delivered milliliter. An exemplary treatment regimen entails administration once per day or once a week. Intervals can also be irregular as indicated by measuring blood levels of glucose or insulin in the subject and adjusting dosage or administration accordingly. In some methods, dosage is adjusted to achieve a desired fasting glucose or fasting insulin concentration. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regimen.

In some embodiments, a therapeutically effective amount of the peptide-based nanofiber precursor composition, peptide-based nanofiber, or carrier complex of the present technology is defined as a concentration of the peptide-based nanofiber precursor composition, peptide-based nanofiber, or carrier complex of the present technology at the target tissue of $10^{-11}$ to $10^{-6}$ molar, e.g., approximately $10^{-7}$ molar. This concentration may be delivered by systemic doses of 0.01 to 100 mg/kg or equivalent dose by body surface area. The schedule of doses is optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and the presence of other diseases. Moreover, treatment of a subject with a therapeutically effective amount of the therapeutic compositions described herein can include a single treatment or a series of treatments.

Combination Therapy with the Compositions of the Present Technology

In some embodiments, the peptide-based nanofiber precursor compositions or peptide-based nanofibers of the present technology or carrier complexes including the same, may be combined with one or more additional therapies for the prevention or treatment of breast cancer, brain cancer, ovarian cancer or prostate cancer. Additional therapeutic agents or active agents include, but are not limited to, anastrozole, bevacizumab, capecitabine, carboplatin, denosumab, docetaxel, doxorubicin, doxil, aldoxorubicin, eribulin, exemestane, fluorouracil, fulvestrant, gemcitabine, ixabepilone, lapatinib, letrozole, methotrexate, paclitaxel, trastuzumab, tamoxifen, cisplatin, cyclophosphamide, abiraterone acetate, cabazitaxel, leuprolide, Radium-223 dichloride, sipuleucel-T, bicalutamide, degarelix, enzalutamide, flutamide, goserelin acetate, leuprolide acetate, and mitoxantrone hydrochloride.

In any case, the multiple therapeutic agents may be administered in any order or even simultaneously. If simultaneously, the multiple therapeutic agents may be provided in a single, unified form, or in multiple forms (by way of example only, either as a single pill or as two separate pills).

One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

EXAMPLES

The present technology is further illustrated by the following examples, which should not be construed as limiting in any way.

Example 1. General Methods and Materials

Chemicals and Supplies.

All of the protected amino acids, resins, and solvents for peptide synthesis were purchased from Protein Technologies Inc. (Tucson, Ariz.). Trifluoroacetic acid (TFA), thioanisole, anisole, methyl-tert-butyl ether, N,N-diisopropylethylamine (DIPEA), and hydrazine were obtained from Sigma-Aldrich (St. Louis, Mo.). N2'-deacetyl-N2'-(3-mercapto-1-oxopropyl)-maytansine (DM1) was supplied by Carbosynth Ltd. (Compton, WB). CathB (purified from bovine spleen) and CathB inhibitor II were obtained from EMD Millipore (Billerica, Mass.). Uranyl formate was purchased from Electron Microscopy Sciences (Hatfield, Pa.). Sulfosuccinimidyl 4-[N-maleimidomethyl] cyclohexane-1-carboxylate (sulfo-SMCC), 4'6-diaminidino-2-pheylindole (DAPI), and LysoTracker Red were obtained from Life Technologies Inc. (Norwalk, Conn.).

Peptide Synthesis.

Peptide synthesis and mPEG conjugation were performed on rink-amide resin employing the traditional N-α-Fmoc methodology, previously described in Law et al., *Bioconjug Chem* 18:1701-1704 (2007). After peptide elongation and mPEG coupling, the 1-(4,4-dimethyl-2,6-dioxocyclohexylidene)3-methylbutyl (ivDde) side-chain protection group of C-terminal lysine was selectively removed with hydrazine (2% w/w) in dimethylformamide (DMF). For fluorophore conjugation, FITC (97.3 mg, 5 equiv) in DMSO (4 mL) or Cy5.5 NHS ester (50 mg, 1.4 equiv) in DMF (4 mL) was added to resin (0.05 mmoL, 1 equiv) in the presence of DIEPA (1 mL) overnight. The peptides were cleaved from the resin using a cleaving cocktail (5 mL) composed of TFA/thioanisole/water/anisole (90:5:3:2) and then precipitated in methyl-tert-butyl ether and purified by reverse-phase high-performance liquid chromatography (rp-HPLC).

Conjugation of DM1 to the Peptide Constructs.

After the removal of the ivDde side-chain protection group of the C-terminal lysine, as described above, sulfo-SMCC (25 mg, 1 equiv) in Nmethylpyrrolidone (NMP; 4 mL) was then added to the resin (0.05 mmoL, 1 equiv) and allowed to react overnight. The peptides were separated from the resin using the cleaving cocktail (5 mL) and then precipitated and purified by rp-HPLC. DM1 (1 mg, 1 equiv) was added to the resulting MCC-peptides (10 mg, 3 equiv) in a cosolvent of NMP (100 µL) and phosphate-buffered saline (PBS; 10 mM, pH 7,100 µL) and allowed to react for 2 days at room temperature. The final DM1-MCC-peptide constructs were purified by rp-HPLC. All the peptides and their intermediates were characterized according to their average molecular weights using MALDI-TOF analysis (Tufts Medical School, Core Facility, Boston, Mass.).

Nanofiber Assembly.

Nanofibers were assembled using the solvent evaporation method (Malik et al., *Anal Biochem.* 412 26-33 (2011)). Briefly, peptide constructs (0.5 mg) in dimethyl sulfoxide (DMSO; 10 µL) were added to a cosolvent of acetonitrile and water (1.5 mL). The assembled nanofibers were purified by size exclusion chromatography (Sephadex G-25) to remove the free peptides and then homogenized into 100 nm lengths using a mini-extruder (Avanti Polar Lipids, Alabaster, Ala.) and polycarbonate membrane of the appropriate pore size (Whatman, Maidstone, U.K.). The concentration of NFP1 and NFP2 nanofibers was determined by ultraviolet (UV) absorbance according to the extinction coefficient of Cy5.5 (209,000 $cm^{-1}$ $M^{-1}$) or FITC (60,000 $cm^{-1}$ $M^{-1}$) in 5% (v/v) PBS in methanol.

Enzyme Digestion Study.

NFP1 and NFP2 nanofibers (50 µM of peptide content) were incubated with CathB (0.3 U) in sodium acetate buffer (50 µM; pH 4). Nanofibers incubated with buffer only were used as the negative controls. After 24 hours, the samples were taken out for TEM, rp-HPLC, and MALDI-TOF analysis. For the inhibition study, CathB inhibitor II (100 µM) was added to the samples during incubation.

Transmission Electron Microscopy.

Intact or digested NFP1 and NFP2 nanofibers (10 µM of peptide content) in buffer (20 µL) were transferred onto Formvar/carbon-coated 400 mesh copper grids (Electron Microscopy Sciences, Hatfield, Pa.). Excess nanofibers were blotted off using filter paper and the samples were stained with 0.5% (v/v) uranyl formate solution (20 µL). After drying at room temperature, the grids were examined under TEM (JEOL JEM-1400 LaB6 TEM operating at 120 Kv).

Cell Cultures.

All supplies for cell cultures were purchased from Corning Cellgro Inc. (Tewksbury, Mass.). The cell lines (ATCC, Manassas, Va.) were cultured in an RPMI 1640 medium supplemented with 10% (v/v) fetal bovine serum (FBS), penicillin (50 000 units/L), and streptomycin (50 mg/L), and then maintained in 5% of $CO_2$ at 37° C.

Fluorescence Microscopy.

Cells ($3 \times 10^3$/well) were seeded on an 8-well chamber slide until they reached 60% confluency. To study the cellular distribution, NFP1 and NFP2 nanofibers (10 µM of peptide content) were added to the cells for 6 hours at 37° C. Prior to microscopic imaging, DAPI (9 µM) and LysoTracker Red (1 µM) were added to the culture medium to stain the nucleus and lysosomes, respectively. Cells were then washed with PBS. Images were acquired with an EVOS FL Auto Fluorescence Microscope (Life Technologies) using the appropriate excitation and emission filters. To investigate the release of fluorophores intracellularly, the cells were first incubated with NFP1 or NFP2 nanofibers for 6 hours. The culture medium was then replaced with fresh medium. Images were acquired at 0 and 24 hours. For control experiments, lysosomal catabolic functions were inhibited by adding ammonium chloride (100 mM) to the culture medium 2 hours prior to incubation with NFP1 or NFP2 nanofibers.

Cytotoxicity Assay.

The cytotoxicity of drug-loaded NFP1 and NFP2 nanofibers was assessed using the CellTiter-Glo Luminescent Cell Viability Assay (Promega, Madison, Wis.) as previously described in Junttila et al., *Breast Cancer Res. Treat.* 128 (2), 347-356 (2011). Briefly, cells were seeded on a 96-well plate ($2 \times 10^3$/well for MDA-MB-231 and MDA-MB-468 and $2 \times 10^4$/well for BT474) and were allowed to stabilize overnight. The culture medium was then replaced with fresh media containing different concentrations of nanofibers, free DM1, or T-DM1 (Genentech, South San Francisco, Calif.) according to the DM1 content (100 pM to 10 μM). After 5 days of incubation, CellTiter-Glo reagent (100 μL) was added to each well. The generated oxyluciferin was quantified for emitted luminescence using a microplate reader (Tecan US Inc., Morrisville, N.C.). All experiments were performed in triplicate, and the results were presented as mean±standard deviation. Statistical analyses were performed using Graph Pad Prism 6.0 software. All data were normalized to the values obtained with the untreated control cells, and half maximal inhibitory concentrations ($IC_{50}$) were calculated by fitting the obtained data to a sigmoidal curve.

Example 2. The Design and Synthesis of NFP1 and NFP2

Figure 2A:
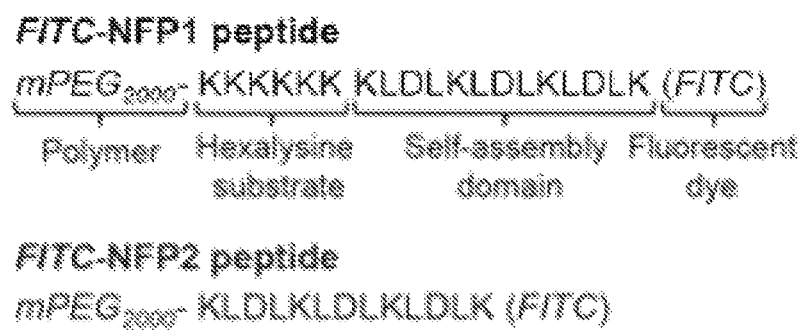
FIG. 2A shows the amino acid sequences of the peptide constructs used for assembling the nanofibers. Each of these peptide constructs comprise a self-assembling domain conjugated with a hydrophilic mPEG$_{2000}$ chain and a FITC fluorophore. Unlike FITC-NFP2 (SEQ ID NO: 1), FITC-NFP1 (SEQ ID NO: 4) includes a hexalysine motif (SEQ ID NO: 13).

NFP1 and NFP2 nanofibers are composed of multiple peptides, wherein each peptide contains a self-assembling domain having the sequence KLDLKLDLKLDLK (SEQ ID NO: 1). Further, each individual peptide was conjugated to a 2 kDa mPEG polymer at its N-terminus and a FITC fluorophore at its C-terminus. The amino acid sequences of the NFP1 and NFP2 peptide constructs are shown in FIG. 2A. The peptide constructs could self-assemble into nanofibers in PBS.

Multiple peptide constructs could self-assemble into a single-layer structure in aqueous media, which can be further homogenized into 100 nm lengths using a miniextruder.

Figure 2B:
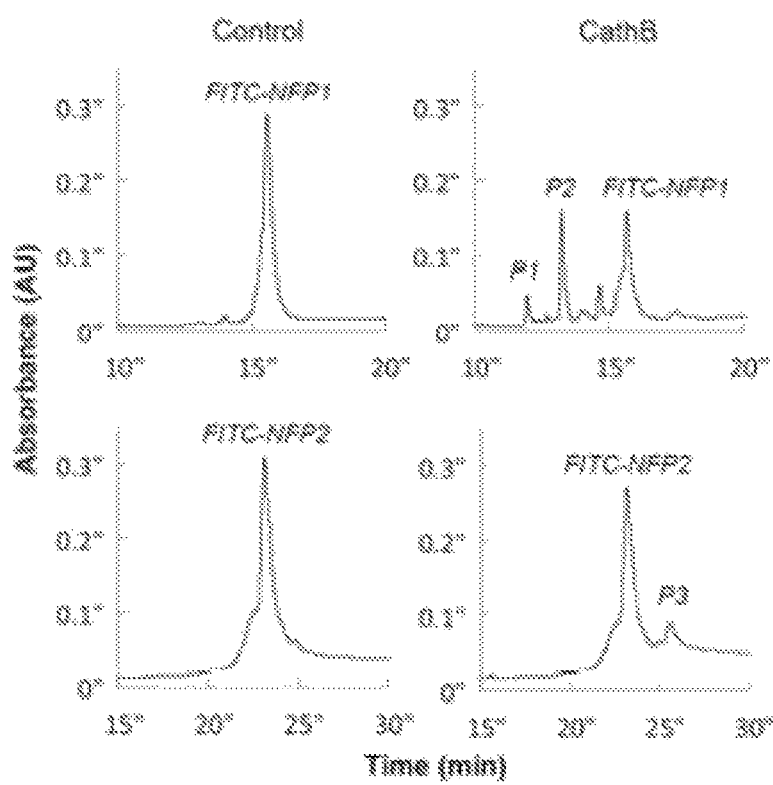
FIGS. 2B and 2C show a comparison of the CathB cleavage of FITC-labeled NFP1 (FITC-NFP1) and NFP2 (FITC-NFP2).
Figure 2C:
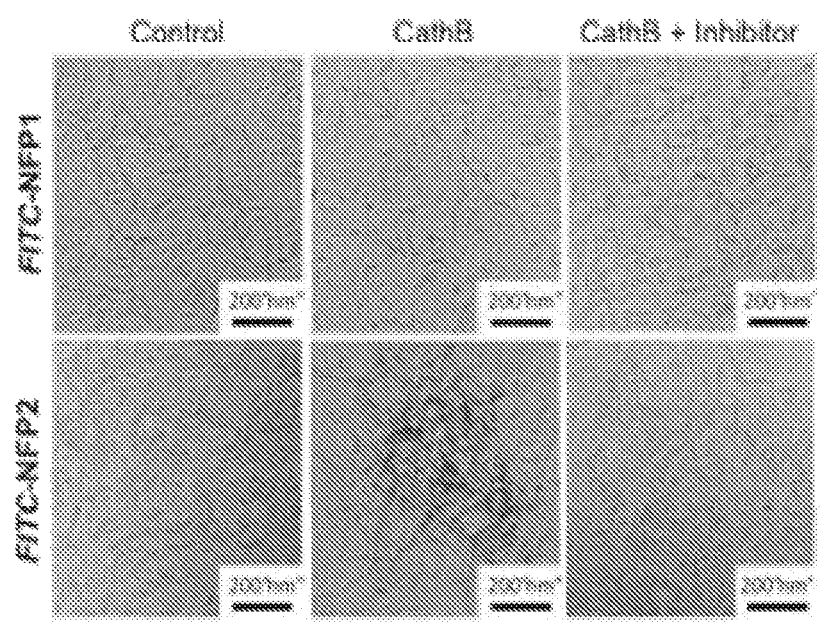

NFP1 and NFP2 peptides are composed of L-amino acids and can be cleaved by CathB at or near the lysine residues located within the self-assembling domain. Unlike NFP2, NFP1 also contains a hexalysine motif (SEQ ID NO: 13) (FIG. 2A). As shown in FIGS. 2B and 2C, NFP1 showed increased sensitivity to CathB digestion compared to NFP2.

NFP1 and NFP2 peptides are stabilized by strong hydrophobic and electrostatic interactions, thus permitting the incorporation of fluorophores, antibodies, and peptide moieties without affecting the final morphology of the nanofibers. As such, the peptide-based nanofiber precursor compositions of the present technology are capable of forming nanofiber structures, either by themselves or when conjugated/complexed with fluorophores, antibodies, or peptide moieties. As such, the compositions of the present technology are useful in methods for delivering a payload (e.g., a therapeutic or diagnostic agent) to a cancerous cell.

Example 3. Comparison of Enzymatic Cleavage Observed with FITC-NFP1 and FITC-NFP2

HPLC analysis showed that CathB digested FITC-NFP1 into multiple peptide fragments after 24 hours (FIG. 2B). To determine the CathB cleavage sites within the NFP1 and NFP2 peptide constructs, HPLC elution peaks were collected for further MALDI-TOF analysis.

Multiple enzymatic cleavage sites located at the hexalysine motif and the self-assembling domain of FITC-NFP1 were identified based on the molecular weight differences between the peptide fragments and the undigested peptide construct. Cleavage mainly occurred at the lysine residues with the exception of one cleavage site between a leucine and an aspartic acid (Table 1).

TABLE 1

Identified Intact or Digested Peptide Fragments of FITC-NFP1 and FITC-NFP2 after CathB Cleavage

| Peak | Molecular Weight (Da) | Amino Acid Sequence |
|---|---|---|
| FITC-NFP1 | avg. 4637 | $mPEG_{2000}$ KKKKK ¦ KK ¦ LDLKLD ¦ L ¦ KLDL ¦ K ¦ (FITC) (SEQ ID NO: 4) |
| P1 | 830 | LDLKLDL (SEQ ID NO: 2) |
|  | 1554 | KKLDLKLDLKLDL (SEQ ID NO: 3) or KLDLKLDLKLDLK (SEQ ID NO: 1) |
| P2 | avg. 3519 | $mPEG_{2000}$ KKKKKKKLDLKLD (SEQ ID NO: 5) |
|  | avg. 4247 | $mPEG_{2000}$-KKKKKKKLDLKLDLKLDLK (SEQ ID NO: 4) |
| FITC-NFP2 | avg. 3866 | $mPEG_{2000}$ ¦ KLDLKLDLKLDLK(FITC) (SEQ ID NO: 1) |
| P3 | 1944 | KLDLKLDLKLDLK(FITC) (SEQ ID NO: 1) |

*The dashed lines indicate the identified enzyme cleavage sites based on the results of the MALDI-TOF analysis of the collected HPLC peaks.

Figure 8A:
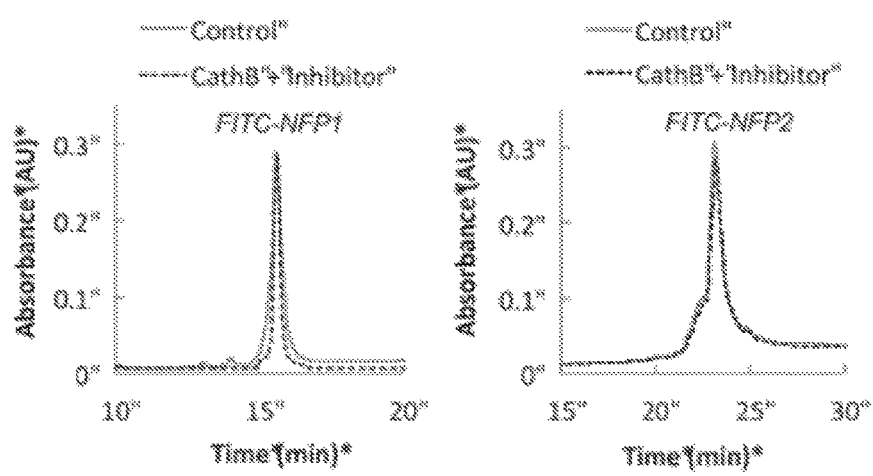
FIG. 8A displays HPLC spectra of FITC-NFP1 and FITC-NFP2 nanofibers (50 µM) that were co-incubated with CathB (0.3 U) and CathB inhibitor (100 µM) in sodium acetate buffer (50 µM, pH 4) for 24 hours at room temperature (which serves as a negative control).

However, only one fragment was identified when FITC-NFP2 was subjected to CathB digestion. This fragment corresponded to a loss of the hydrophilic N-terminal mPEG chain of the peptide construct (Table 1) and was more hydrophobic, as shown by the broader and red-shifted HPLC peak (FIG. 2B). Using the commercially available CathB inhibitor, it was confirmed that the activations of both FITC-NFP1 and FITC-NFP2 were enzyme specific (FIG. 8A).

Figure 8B:
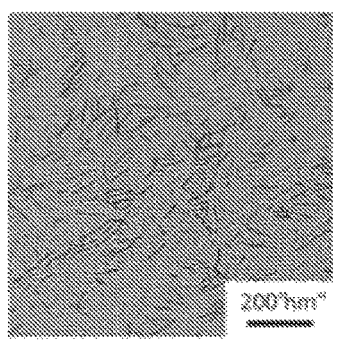
FIG. 8B shows TEM images (80,000× magnification) of nanofibers assembled from KKKKKKKLDLKLDLKLDLK(FITC) (SEQ ID NO: 4). The sample was stained with uranyl formate (0.5% v/v) before analysis.

The morphological changes of NFP1 and NFP2 fibers in response to CathB digestion were evaluated. TEM studies revealed that after a 24 hour incubation with the enzyme, FITC-NFP1 disintegrated and became shorter in length (FIG. 2C). The hydrophilic lysine residues in the hexalysine motif (SEQ ID NO: 13) of FITC-NFP1 blocked aggregation, even in the absence of the mPEG chain (FIG. 8B), thus permitting complete CathB digestion.

In contrast, multiple FITC-NFP2 fibers assembled into an interfibril network (FIG. 2C). This interfibril network may show increased resistance to CathB digestion relative to that observed with FITC-NFP1 fibers. Thus, these results demonstrate that compositions including NFP2 peptides are useful for prolonging the storage of fluorophores, or other diagnostic agents (magnetic contrast agents, radiotracers etc.) within lysosomes (See FIGS. 4A and 4B during cell labeling and imaging applications.

Accordingly, these results demonstrate that the peptide-based nanofiber precursor compositions or peptide-based nanofibers of the present technology are useful in methods for delivering a payload (e.g., a therapeutic or diagnostic agent) to a cancerous cell.

Example 4. Optimization of the Optical Properties of NFP1 and NFP2 for Cell Imaging Studies The unique digestion profile of NFP1 and NFP2 suggested that these nanofibers might exhibit distinctive behavior in cells where there is abundant amount of CathB, particularly inside the lysosomes. To evaluate cellular distribution, Cy5.5 fluorophore was incorporated into NFP1 and NFP2 to perform imaging studies by fluorescence microscopy.

Figure 3A:
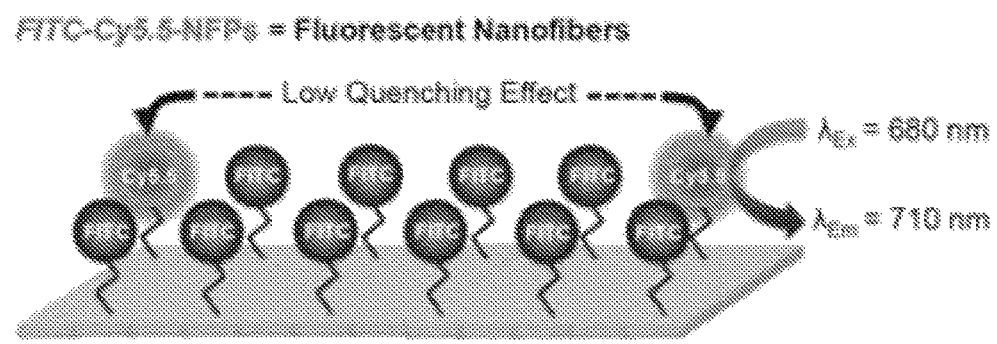
FIGS. 3A-3D show the optimization of the optical properties of NFP1 and NFP2 for cellular imaging experiments.

However, incorporating substantial amounts of the Cy5.5 fluorophore into NFP1 and NFP2 caused fluorescence quenching. To control the Cy5.5 loading, we used a comixture of Cy5.5-conjugated and FITC-conjugated peptide constructs (serving as the spacer) at different ratios (1:0, 1:9, and 1:19) during the nanofiber assembly process (FIG. 3A). Successful synthesis of these nanofibers was confirmed by UV absorbance and TEM analysis (FIG. 9).

Figure 9A:
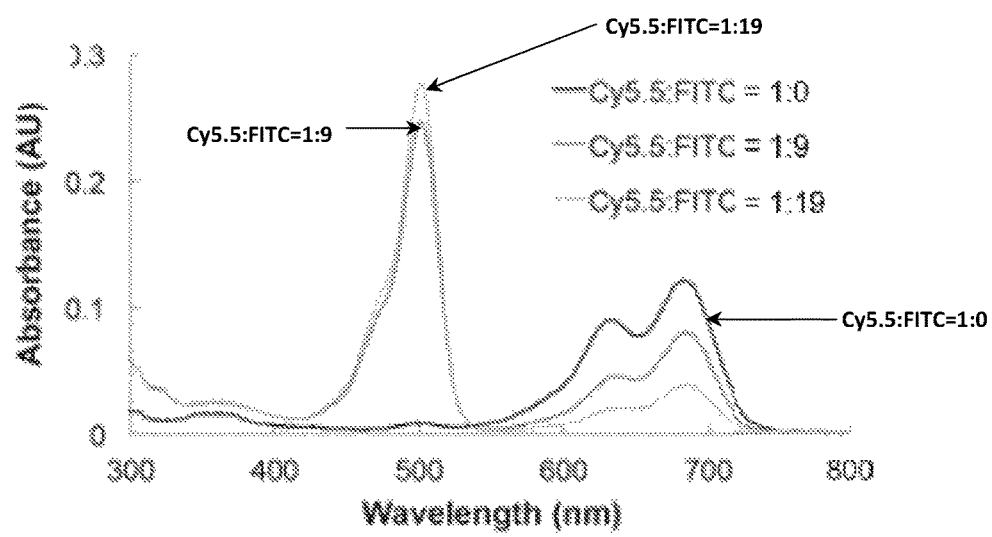
FIG. 9A displays UV absorption spectra confirming the formation of quenched Cy5.5 NFP1 (ratio Cy5.5:FITC=1:0) and Cy5.5-FITC-NFP1 (ratio Cy5.5:FITC=1:9 and 1:19). Measurements were performed in 5% (v/v) PBS in methanol. The maximum absorption $\lambda_{max}$ of FITC and Cy5.5 was 495 nm and 680 nm, respectively.
Figure 9B:
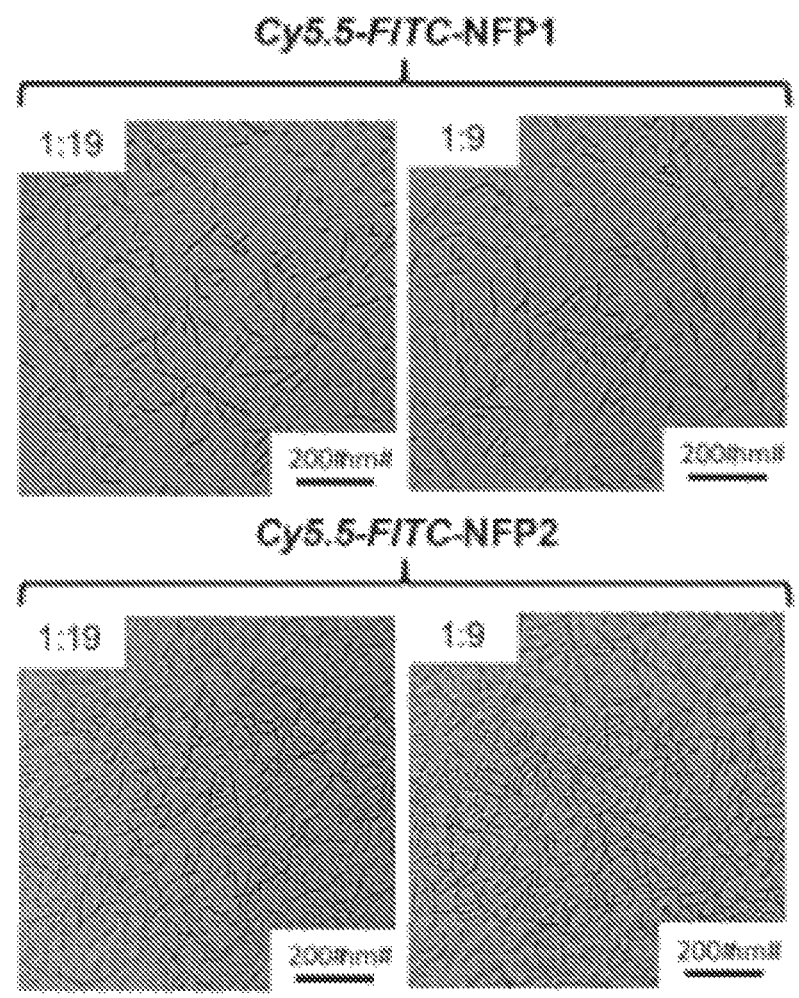
FIG. 9B shows TEM images of Cy5.5-FITC-NFP1 and Cy5.5-FITC-NFP2 incorporated with different ratios of Cy5.5 and FITC (1:19 and 1:9).

To identify the formulations with a minimal quenching effect, fluorescent NFP1 and NFP2 nanofibers having different ratios of Cy5.5 and FITC were prepared, and their optical properties were analyzed by UV absorbance and TEM (FIGS. 9A and 9B). Cy5.5-FITC-NFP1 and Cy5.5-FITC-NFP2 containing Cy5.5 and FITC at a molar ratio of 1:19 exhibited fluorescence emission at 710 nm (FIG. 3C), suggesting that these compositions could be used for directly assess cellular uptake and localization of nanofibers.

Figure 3B:
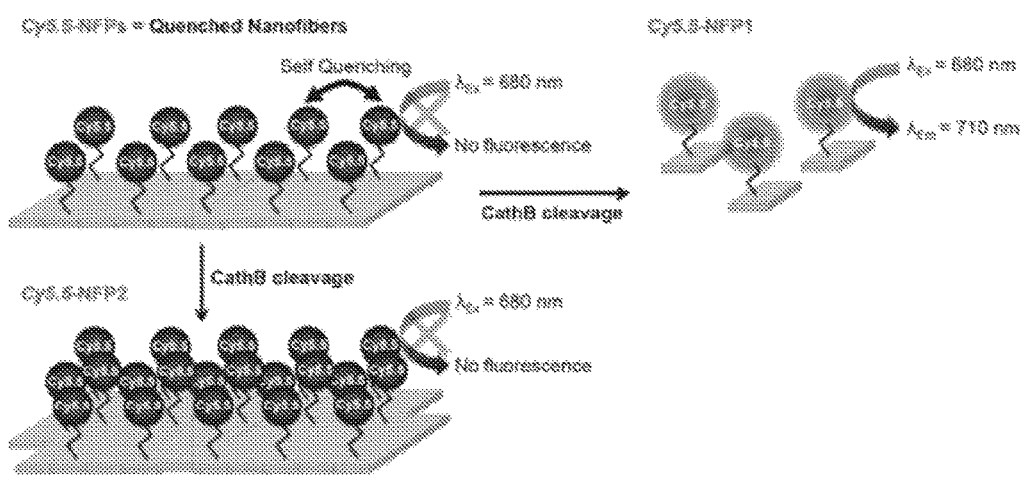
Figure 3C:
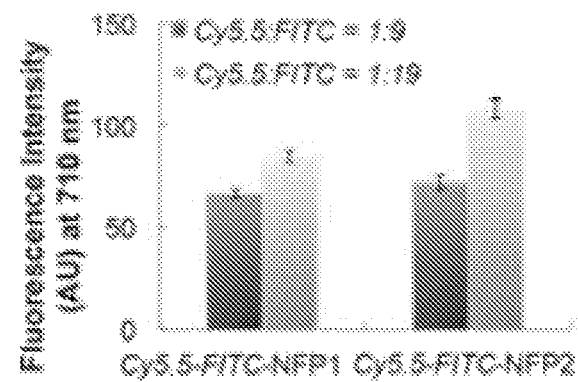
Figure 3D:
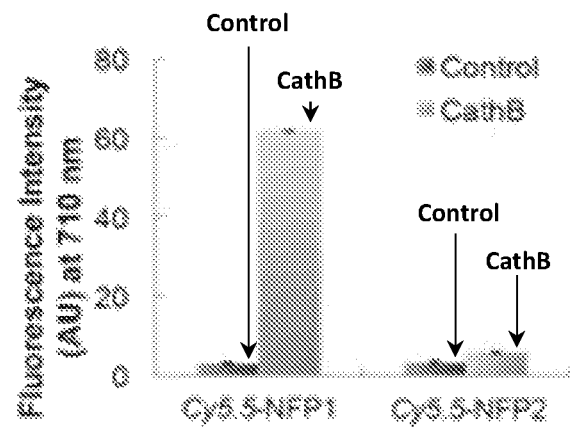
Figure 9C:
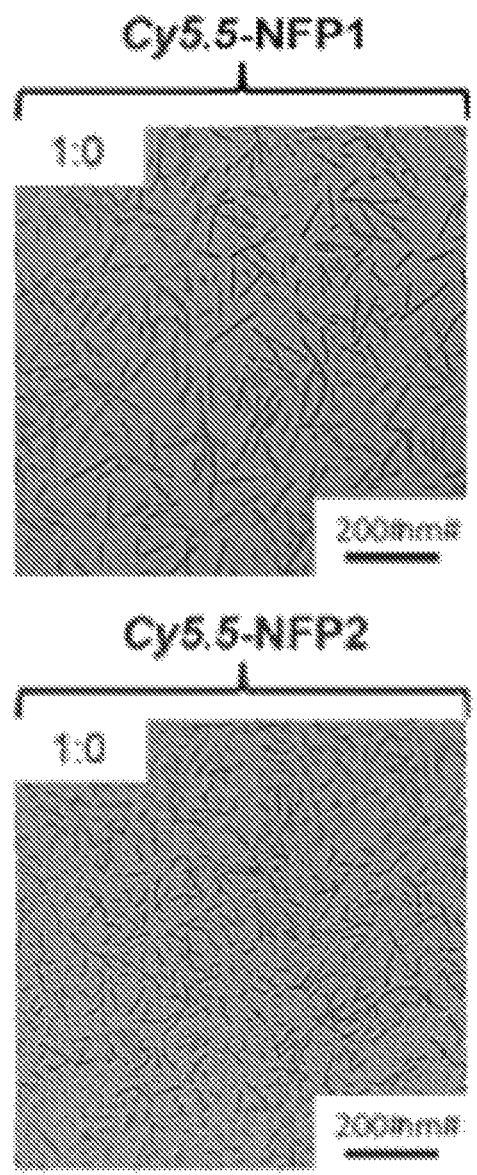
FIG. 9C shows TEM images of Cy5.5-NFP1 and Cy5.5-NFP2 (ratio Cy5.5:FITC=1:0). All samples were stained with uranyl formate (0.5% v/v) prior to TEM analysis with a magnification of 80,000×.

NFP1 and NFP2 formulations that were optically silent in their native state were prepared using Cy5.5-conjugated peptide constructs only (FIG. 3B and FIGS. 9A and 9C). Cy5.5-NFP1 and Cy5.5-NFP2 were completely quenched prior to CathB digestion. As shown in FIG. 3D, CathB digestion of Cy5.5-NFP1 led to the release of Cy5.5-peptide fragments, thus resulting in the recovery of the fluorescence signal. These results demonstrate that CathB-induced changes in fluorescence are useful for monitoring the lysosomal degradation of NFP1 and that compositions including NFP1 peptides are useful in methods for delivering a payload (e.g., a therapeutic agent) to a cancerous cell.

In contrast, the fluorescence of Cy5.5-NFP2 was only slightly increased after exposure to CathB, indicating that NFP2 is retained within the lysosomes. See FIG. 3D. Thus, these results demonstrate that compositions including NFP2 peptides are useful for prolonging the storage of fluorophores, or other diagnostic agents (magnetic contrast agents, radiotracers etc.) within lysosomes (See FIGS. 4A and 4B) during cell labeling and imaging applications.

Accordingly, these results demonstrate that the peptide-based nanofiber precursor compositions or peptide-based nanofibers of the present technology are useful in methods for delivering a payload (e.g., a therapeutic or diagnostic agent) to a cancerous cell.

Example 5. Intracellular Delivery of NFP1 and NFP2

Figure 4A:
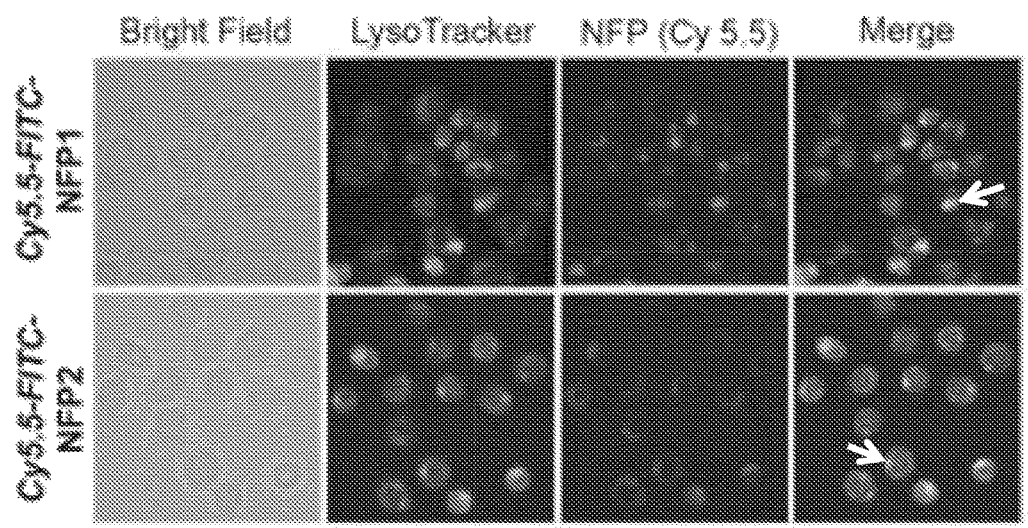
FIGS. 4A and 4B show a comparison of the cellular distribution and degradation of NFP1 and NFP2.
Figure 10:
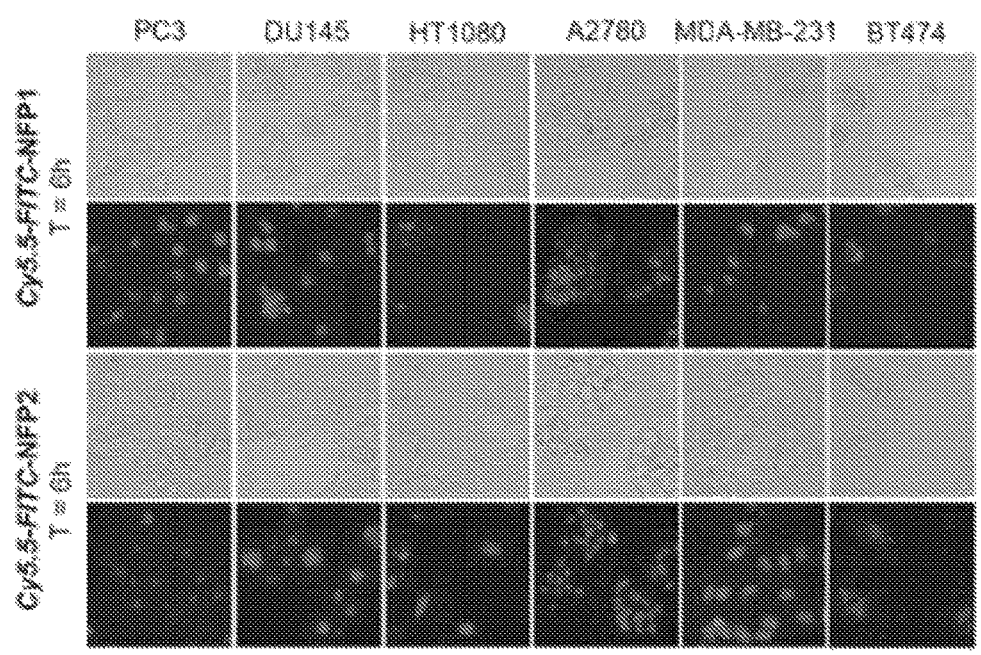
FIG. 10 shows fluorescence images of different cancer cell lines incubated with Cy5.5-FITC-NFP1 and Cy5.5-FITC-NFP2 (10 µM of peptide content) for 6 hours. DAPI (9 µM) was added to the culture medium 30 minutes prior to fluorescence imaging for nuclei visualization. Both fluorescent Cy5.5-FITC-NFP1 and Cy5.5-FITC-NFP2 were internalized into breast, ovarian, and prostate cancer cell lines after 6 hours of incubation.
Figure 11A:
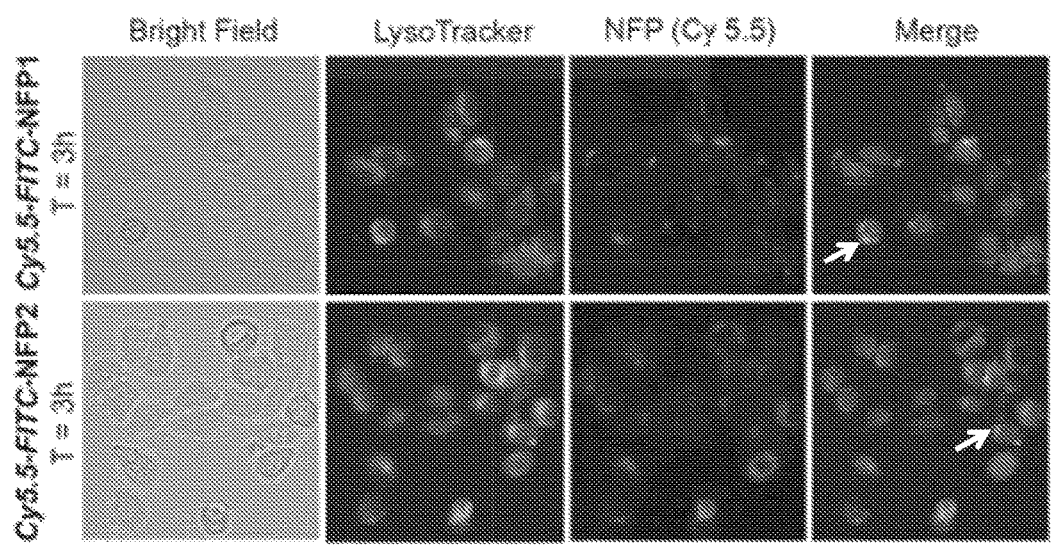
FIG. 11A shows the cellular distribution of Cy5.5-FITC-NFP1 and Cy5.5-FITC-NFP2 (10 µM of peptide content). The MDA-MB-468 cells were incubated with the nanofibers for 3 hours.

As shown in FIG. 10, both Cy5.5-FITC-NFP1 and Cy5.5-FITC-NFP2 could internalize into various breast, ovarian, and prostate cancer lines. Using the human triple negative breast cancer (TNBC) cell line MDA-MB-468 as the cell model, Cy5.5-FITC-NFP1 and Cy5.5-FITC-NFP2 nanofibers were found to predominately accumulate in lysosomes (white arrows) after cellular uptake (FIG. 4A and FIG. 11A). Cells treated with Cy5.5-FITC-NFP1 also exhibited Cy5.5 fluorescence throughout the cytoplasm after 3 hours of incubation; presumably because some of the nanofibers were digested by lysosomal CathB to release Cy5.5-peptide fragments. In contrast, Cy5.5-FITC-NFP2 did not show cytoplasmic staining.

Figure 4B:
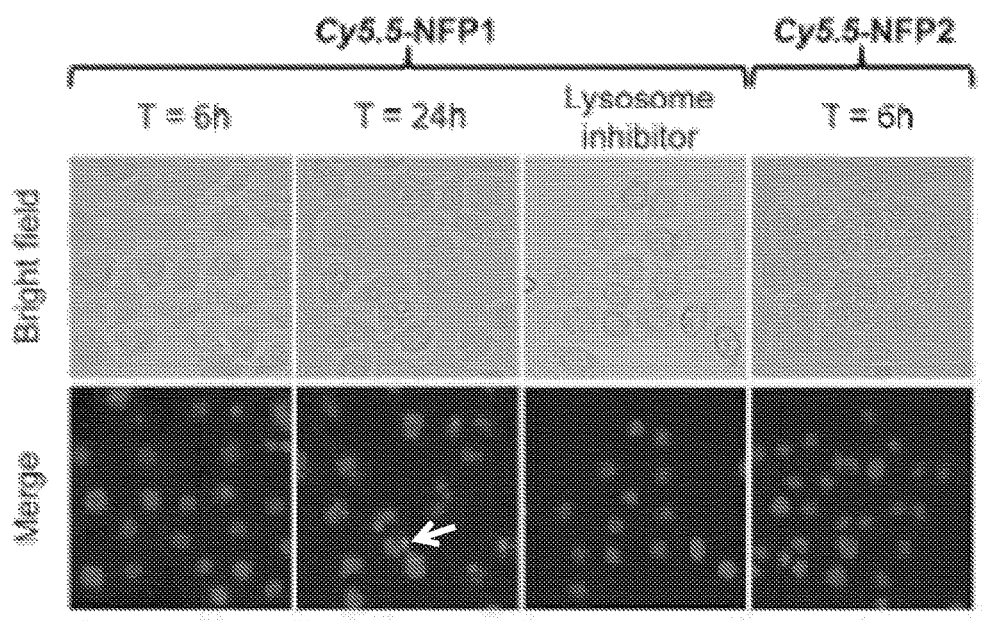
Figure 11B:
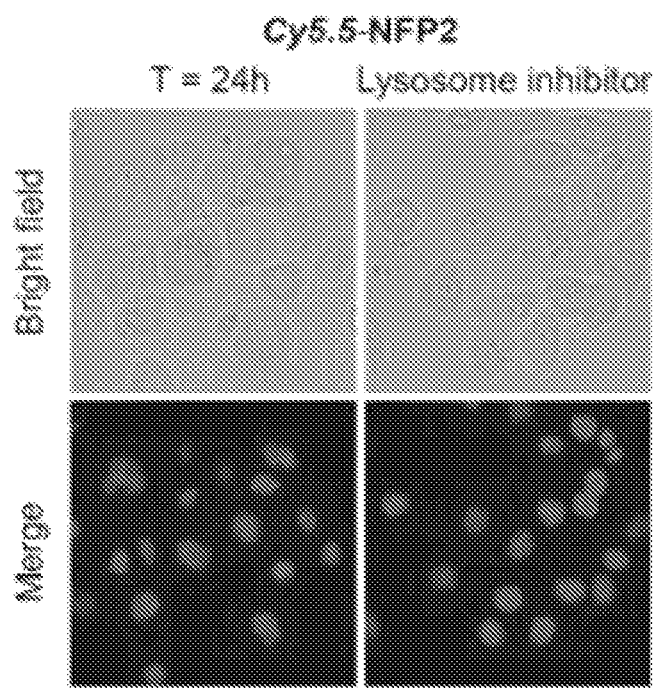
FIG. 11B shows fluorescence images of MDA-MB-468 cells incubated with Cy5.5-NFP2 for 24 hours. Cells pre-incubated with ammonium chloride (100 mM) for 2 hours and then with Cy5.5-NFP2 served as a negative control. DAPI and LysoTracker were added to the culture medium to stain nuclei and lysosomes respectively, at about 30 minutes prior to imaging.

To compare the intracellular degradation of NFP1 and NFP2, cellular imaging studies using the optically quenched Cy5.5-NFP1 and Cy5.5-NFP2 formulations (see FIG. 3B) were performed. Cells pre-incubated with Cy5.5-NFP1 showed an increase in fluorescence over time, indicating that the nanofibers were being degraded (FIG. 4B). Degradation of Cy5.5-NFP1 was lysosome-specific, as shown by the addition of ammonium chloride (an inhibitor of lysosomal function) which inhibited the alterations in fluorescence (FIG. 11B). In contrast, as shown by FIG. 4B and FIG. 11B, no degradation was observed with quenched Cy5.5-NFP2 after 24 hours, presumably because the nanofibers formed lysosomal aggregates that consequently blocked further enzymatic degradation.

These results demonstrate that the peptide-based nanofiber precursor compositions or peptide-based nanofibers of the present technology are useful as carrier complexes. These results also demonstrate that the peptide-based nanofiber precursor compositions or peptide-based nanofibers of the present technology are useful in methods for delivering a payload (e.g., a therapeutic or diagnostic agent) to a cancerous cell.

Example 6. Synthesis and Characterization of DM1-Loaded Nanofiber Formulations

The distinct cellular behaviors and drug release dynamics of NFP1 and NFP2 prompted further investigation into their drug delivery efficiencies. Because NFP1 displayed an antibody-like lysosomal degradation and drug release mechanism, mertansine (DM1), a microtubule polymerization inhibitor that is used as the drug component of an antibody-drug conjugate (T-DM1), was incorporated into the nanofibers to study cytotoxicity.

Figure 5A:
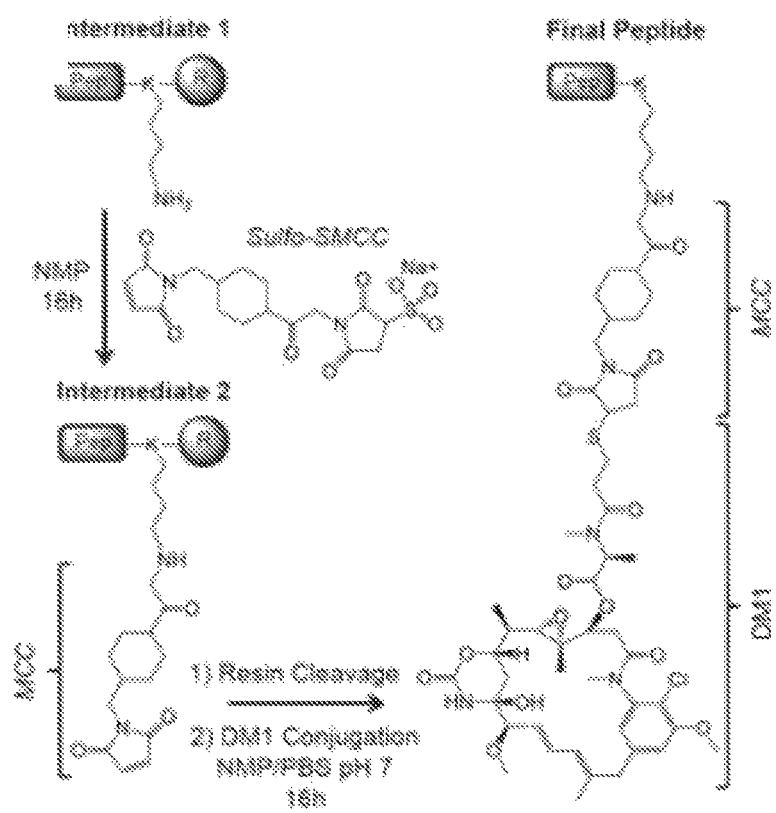
FIGS. 5A and 5B show the synthesis and characterization of DM1-loaded NFP1 (DM1-MCC-NFP1) and NFP2 (DM1-MCC-NFP2).
Figure 5B:
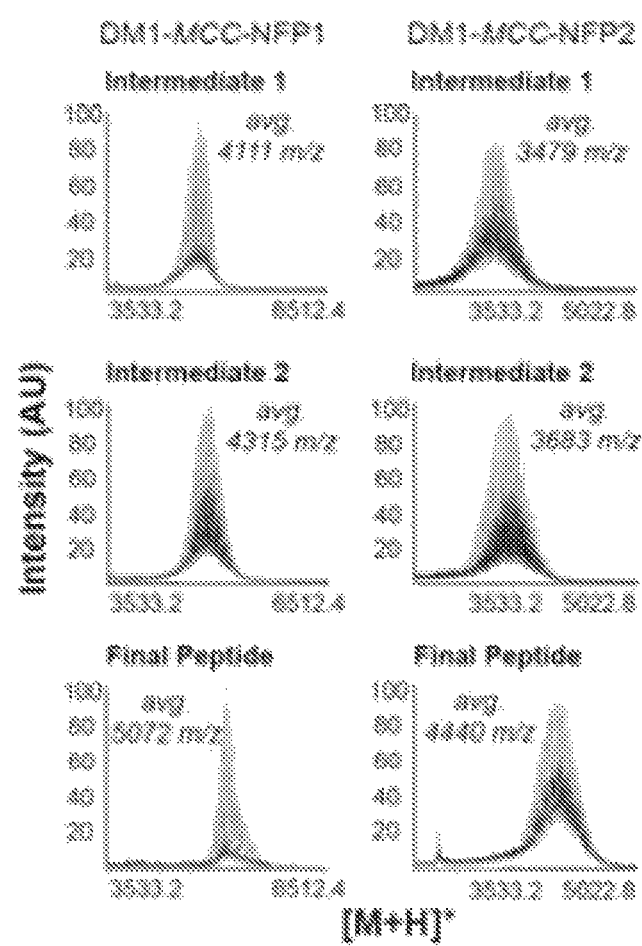

Using the same sulfosuccinimidyl 4-[N-maleimidomethyl]cyclohexane-1-carboxylate (sulfo-SMCC) linker technology to attach DM1 to the antibody, DM1-conjugated NFP1 and NFP2 peptide constructs were prepared by reacting the N-hydroxysuccinimide (NHS) ester of SMCC to the peptides in the solid phase (FIG. 5A). This reaction was performed in the absence of an organic base to avoid the ring opening of the maleimide group, and the introduced SMCC linker was stable under strongly acidic peptide cleavage conditions. Subsequently, DM1 was conjugated to the peptides in solution using the standard thiol-maleimide reaction (FIG. 5A). The synthesis of DM1-MCC-peptide constructs and their intermediates were confirmed by MALDI-TOF analysis (FIG. 5B).

Figure 5C:
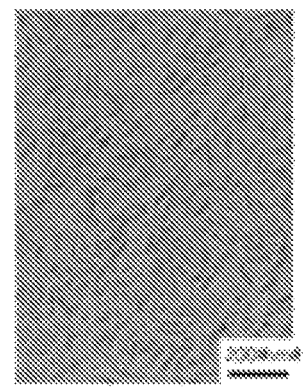
FIG. 5C shows TEM images of the assembled DM1-MCC-NFP1 and DM1-MCC-NFP2. The nanofibers were assembled from a comixture of the corresponding Cy5.5-conjugated and DM1-conjugated peptide constructs at a molar ratio of 1:9.
Figure 5C:
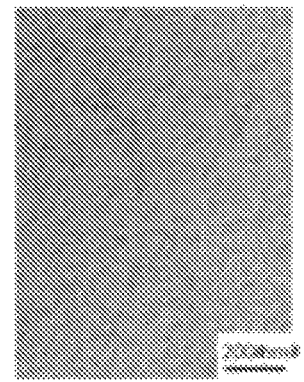

To assemble the DM1-loaded NFP1 (DM1-MCC-NFP1) and NFP2 (DM1-MCC-NFP2), a comixture of the DM1-MCC-peptide and Cy5.5-conjugated peptide constructs at a molar ratio of 9:1 was used. The formation of nanofibers was confirmed by TEM analysis (FIG. 5C).

Based on the absorbance, it was determined that each nanofiber carried approximately 180 DM1 molecules, a significantly larger number than T-DM1 could afford (3.5 DM1 molecules/antibody). See Phillips et al., *Cancer Res.* 68 (22):9280-90 (2008).

Figure 6A:
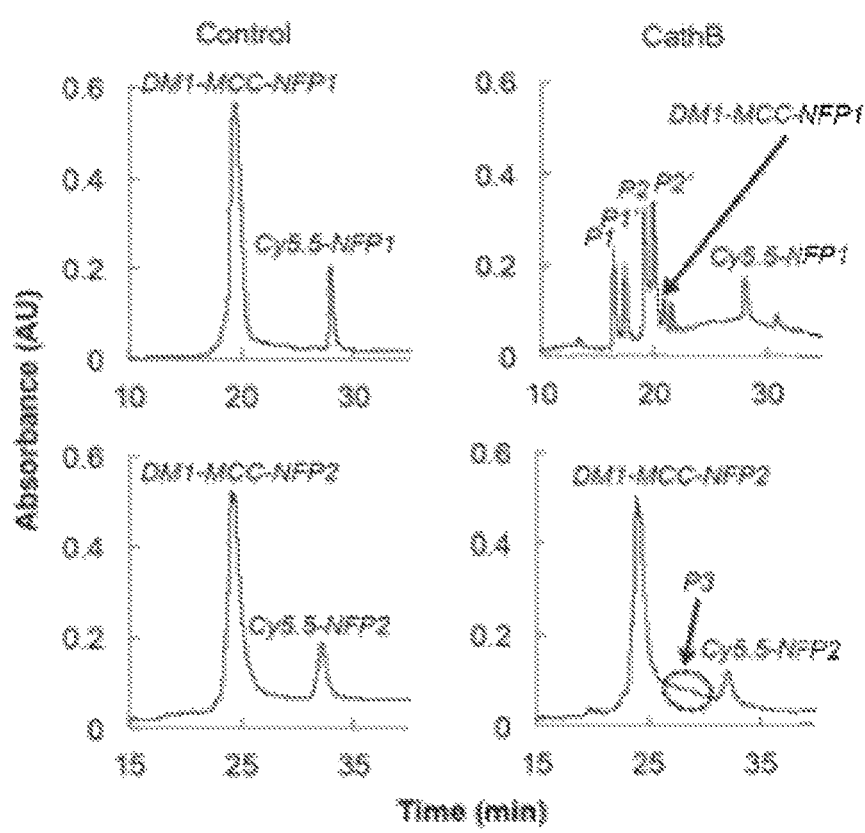
FIGS. 6A and 6B describe the identification of the drug metabolites and peptide fragments of DM1-MCC-NFP1 and DM1-MCC-NFP2 upon CathB activation.
Figure 6B:
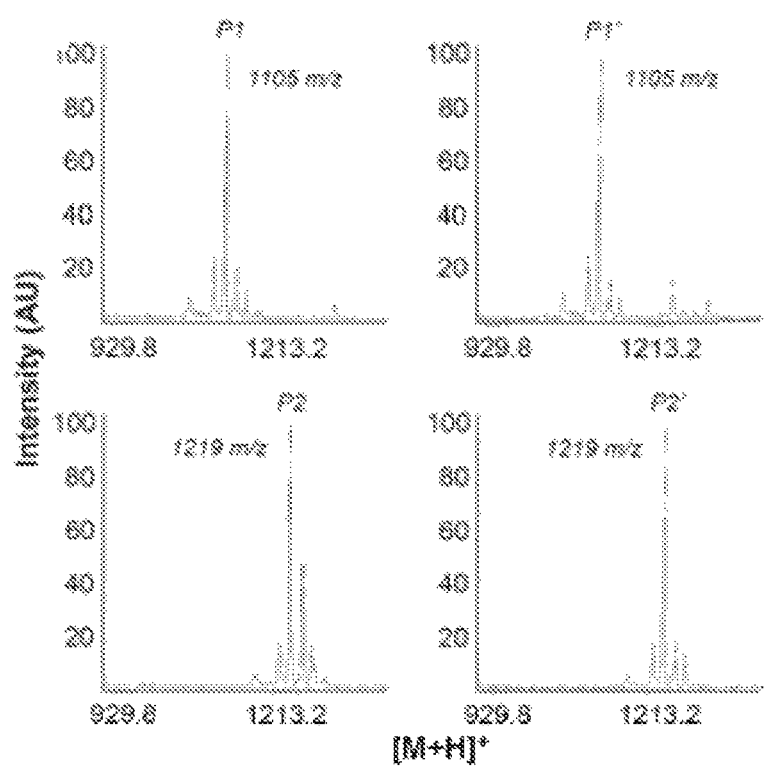

Prior to investigating the cytotoxicity of DM1-MCC-NFP1 and DM1-MCC-NFP2, the CathB-mediated cleavage of both nanofibers was confirmed. After CathB digestion, Lys-MCC-DM1, the same metabolite previously observed as a result of the intracellular degradation of T-DM1, was identified in DM1-MCC-NFP1 (FIG. 6 and Table 2). A second metabolite, Leu-Lys-MCC-DM1 (arising due to the enzymatic cleavage occurring between the leucine and the aspartic acid) was also found. Each drug metabolite had two isomers, as two HPLC peaks were characterized with the same exact molecular mass (FIG. 6B). These isomers were attributed to the R and S configuration at the carbon of the thioether bond formed during the DM1 conjugation.

For DM1-MCC-NFP2, no drug metabolite was identified during CathB digestion due to its slow release property. However, the HPLC spectrum showed a notable aggregation pattern (P3) corresponding to a loss of PEG (FIG. 6A), and this result was confirmed by MALDI-TOF analysis (Table 2).

and MDA-MB-468) cell lines as ex vivo models. A luminescent cell viability assay was employed to determine the cell viability through quantification of the adenosine triphosphate (ATP) produced by metabolically active cells. This assay offered more accurate and reproducible results compared to the widely used MTS assay (data not shown). Because the cell killing of DM1 is slow, the assays were performed following the incubation of the tested samples for 5 days, as previously described in Junttila et al., *Breast Cancer Res. Treat.* 128 (2), 347-356 (2011).

Figure 7A:
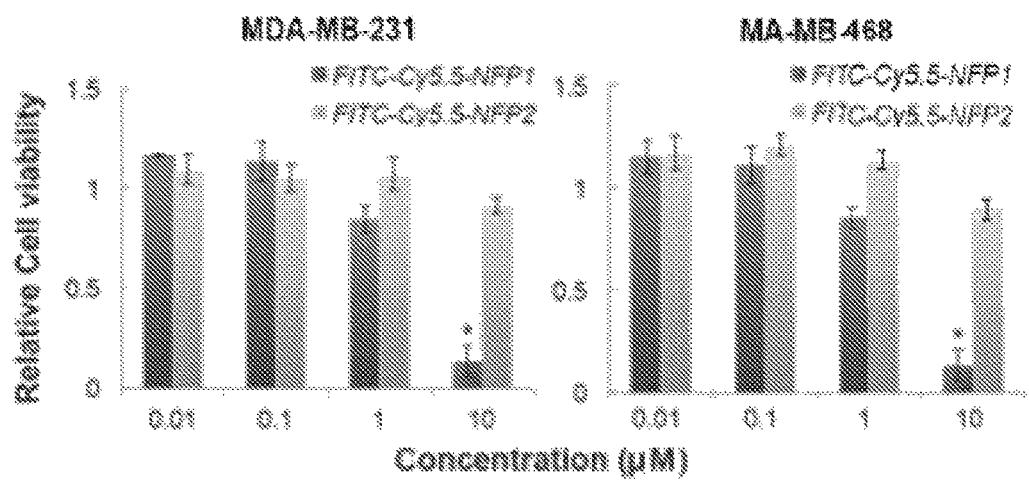
FIGS. 7A and 7B compare the cytotoxicity of the DM1-loaded NFP1 and NFP2 fibers in various human HER2-positive breast cancer (BT474) and triple-negative breast cancer (MDA-MB-231 and MDA-MB-468) cell lines as ex vivo models. Cell viability was measured using the luminescent assay CellTiter-Glo after 5 days of drug treatments.

The toxicity of the naked NFP1 and NFP2 nanofibers was evaluated using MDA-MB-231 and MDA-MB-468 cell lines (FIG. 7A). Below a concentration of 1 µM, both NFP1 and NFP2 were nontoxic. However, NFP1 showed significant cell growth inhibition at a high concentration (10 µM); presumably the multiple positive charges of the hexalysine motif contributed to the toxicity.

Next, the cytotoxicity of the DM1-loaded nanofibers was compared with the antibody-drug conjugate (T-DM1) and

TABLE 2

Identified Drug Metabolites and Peptide Fragments of DM1-MCC-NFP1 and DM1-MCC-NFP2 upon CathB Cleavage

| Peak | Molecular Weight (Da) | Amino acid Sequence |
|---|---|---|
| DM1-MCC-NFP1 | avg. 5072 | mPEG$_{2000}$ KKKKKKKLDLKLD LKLD L K MCC-DM1 (SEQ ID NO: 4) |
| Cy5.5-NFP1 | avg. 4786 | mPEG$_{2000}$-KKKKKKKLDLKLDLKLDLK-Cy5.5 (SEQ ID NO: 4) |
| P1, P1' | 1105 | K-MCC-DM1 |
| P2, P2' | 1219 | LK-MCC-DM1 |
| | avg. 3367 | mPEG$_{2000}$ KKKKKKKLDLKLD (SEQ ID NO: 5) |
| | avg. 4095 | mPEG$_{2000}$-KKKKKKKLDLKLDLKLDLK (SEQ ID NO: 4) |
| DM1-MCC-NFP2 | avg. 4440 | mPEG$_{2000}$ KLDLKLDLKLDLK-MCC-DM1 (SEQ ID NO: 1) |
| Cy5.5-NFP2 | avg. 3955 | mPEG$_{2000}$ KLDLKLDLKLDLK-Cy5.5 (SEQ ID NO: 1) |
| P3 | 2532 | KLDLKLDLKLDLK-MCC-DM1 (SEQ ID NO: 1) |

*The dashed lines indicate the identified enzyme cleavage sites based on the results of the MALDI-TOF analysis of the collected HPLC peaks.

These results demonstrate that the peptide-based nanofiber precursor compositions or peptide-based nanofibers of the present technology are useful as carrier complexes. These results also demonstrate that the peptide-based nanofiber precursor compositions or peptide-based nanofibers of the present technology are useful in methods for delivering a payload (e.g., a therapeutic or diagnostic agent) to a cancerous cell.

Figure 7B:
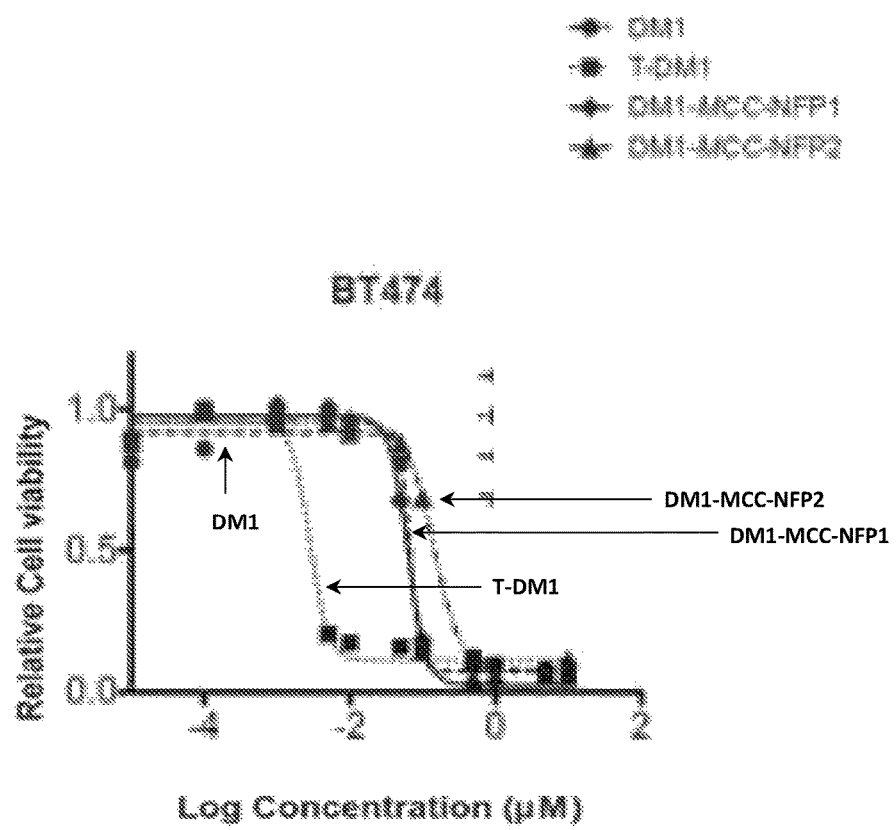
Figure 7B:
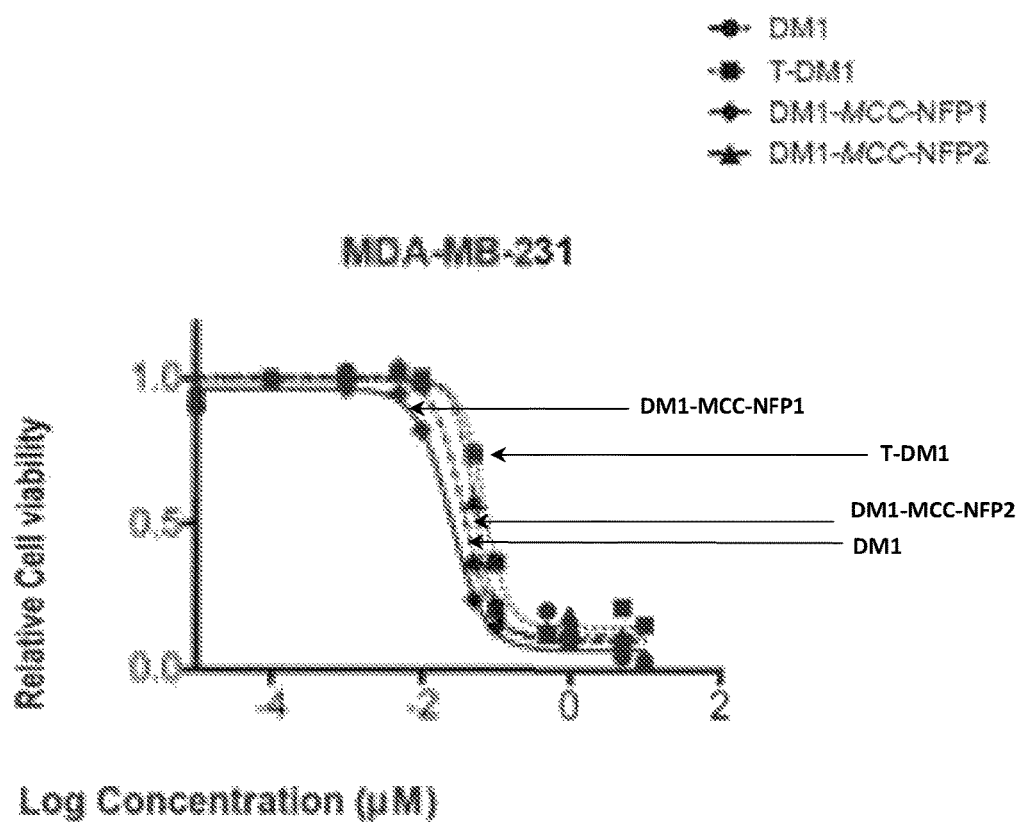
Figure 7B:
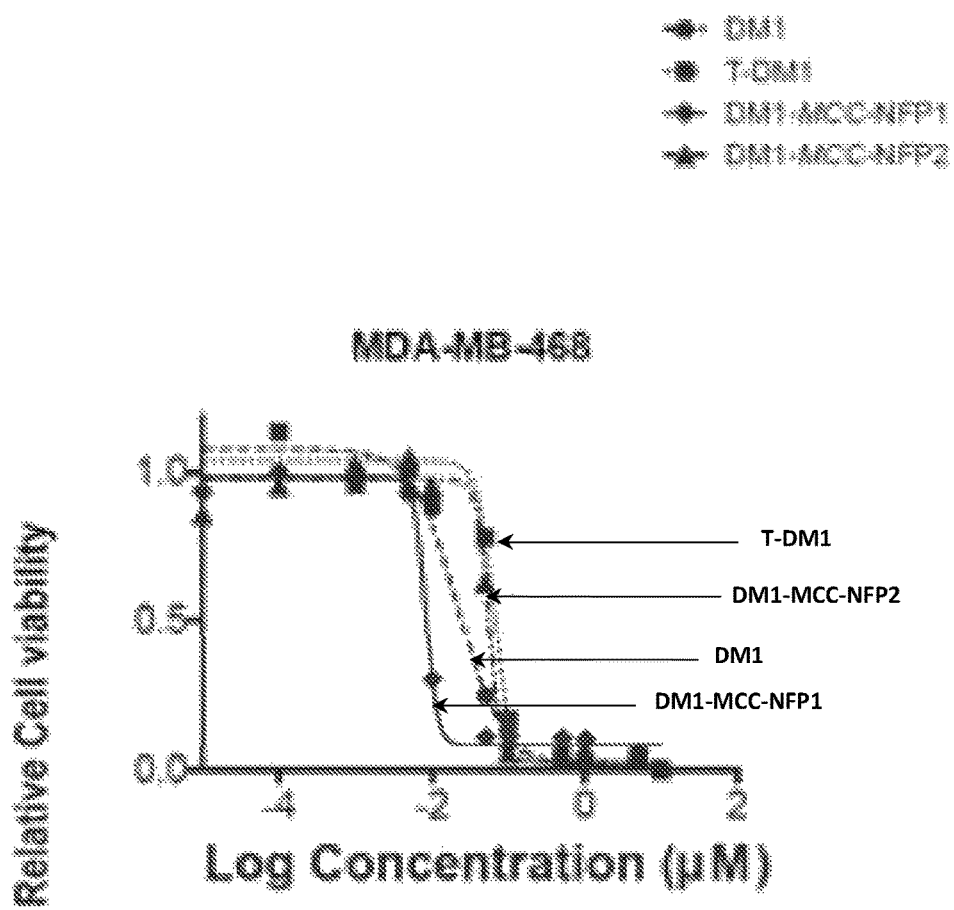

Example 7. Comparison of DM1-MCC-NFP1 and DM1-MCC-NFP2 in the Inhibition of Cancer Cell Growth The cytotoxicity of the DM1-loaded nanofibers was evaluated using various human HER2-positive breast cancer (BT474) and triple-negative breast cancer (MDA-MB-231 the free drug (DM1). T-DM1 was most effective in eradicating HER2-positive BT474 cells (IC$_{50}$=2.8 nM), since it specifically targeted the HER2 receptors for enhanced cellular uptake (FIG. 7B and Table 3). In contrast, DM1-MCC-NFP1 exhibited a higher cytotoxic effect compared to free DM1 toward MDA-MB-231 (IC$_{50}$=24.5 nM) and MDA-MB-468 cells (IC$_{50}$=8.2 nM), which suggested that the nanofibers could be used to deliver cytotoxic agents to TNBC cells. As the naked NFP1 only displayed minimal cell-killing activity at low concentrations, the enhanced cytotoxicity of DM1-MCC-NFP1 may be a result of the increased cellular uptake to subsequently release the active DM1 metabolites via an antibody-like lysosomal degradation mechanism.

TABLE 3

IC$_{50}$ values in human breast cancer cell lines.

| | IC$_{50}$ (nM) | | | |
|---|---|---|---|---|
| | DM1 | T-DM1 | DM1-MCC-NFP1 | DM1-MCC-NFP2 |
| BT474 | 68.1 ± 5.0 | 2.8 ± 0.7 | 62.8 ± 3.1 | 141.7 ± 14.5 |
| MDA-MB-231 | 35.4 ± 4.2 | 68.9 ± 3.8 | 24.5 ± 3.3 | 51.8 ± 2.4 |
| MDA-MB-468 | 21.9 ± 4.1 | 65.2 ± 4.4 | 8.2 ± 0.4 | 55.0 ± 2.7 |

DM1-MCC-NFP2 had a lower but still competitive cytotoxic effect compared to the free DM1 and T-DM1, even though the nanofibers were unable to release the active drug metabolites inside the cancer cells (FIG. 7B and Table 3). Accordingly, these data suggest that both nanofibers could be potentially used for the intracellular delivery of cytotoxic and imaging agents, even though their individual drug release dynamics induce different cell-killing activities.

These results demonstrate that the peptide-based nanofiber precursor compositions or peptide-based nanofibers of the present technology are useful as carrier complexes. These results also demonstrate that the peptide-based nanofiber precursor compositions or peptide-based nanofibers of the present technology are useful in methods for delivering a payload (e.g., a therapeutic or diagnostic agent) to a cancerous cell. Further, these results demonstrate that the peptide-based nanofiber precursor compositions or peptide-based nanofibers of the present technology are useful in methods for inhibiting cancerous cell growth.

Example 8. In Vivo Distribution of the Nanofibers of the Present Technology

Figure 12B:
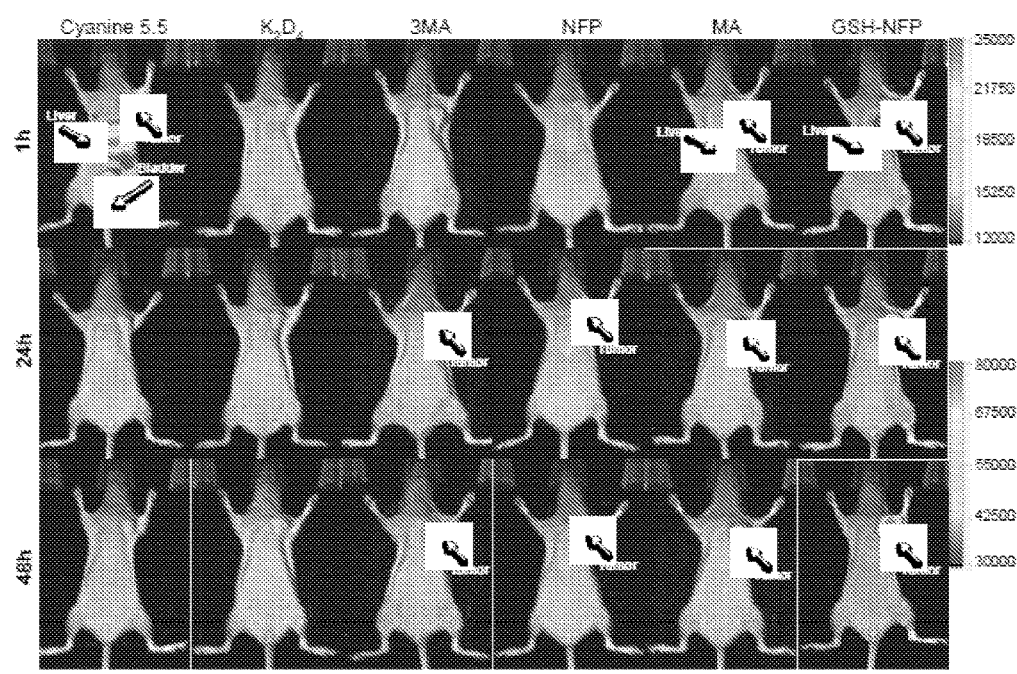
FIG. 12B describes the fluorescence monitoring of nude mice bearing MDA-MB-468 tumors (n=3/group of animal) after tail vein injection of Cyanine 5.5 or nanofibers analogues (0.5 nmol of fluorophore content). GSH-NFP shows significantly higher tumoral uptake compared to Cyanine 5.5 and other nanofiber precursor analogues.
Figure 12C:
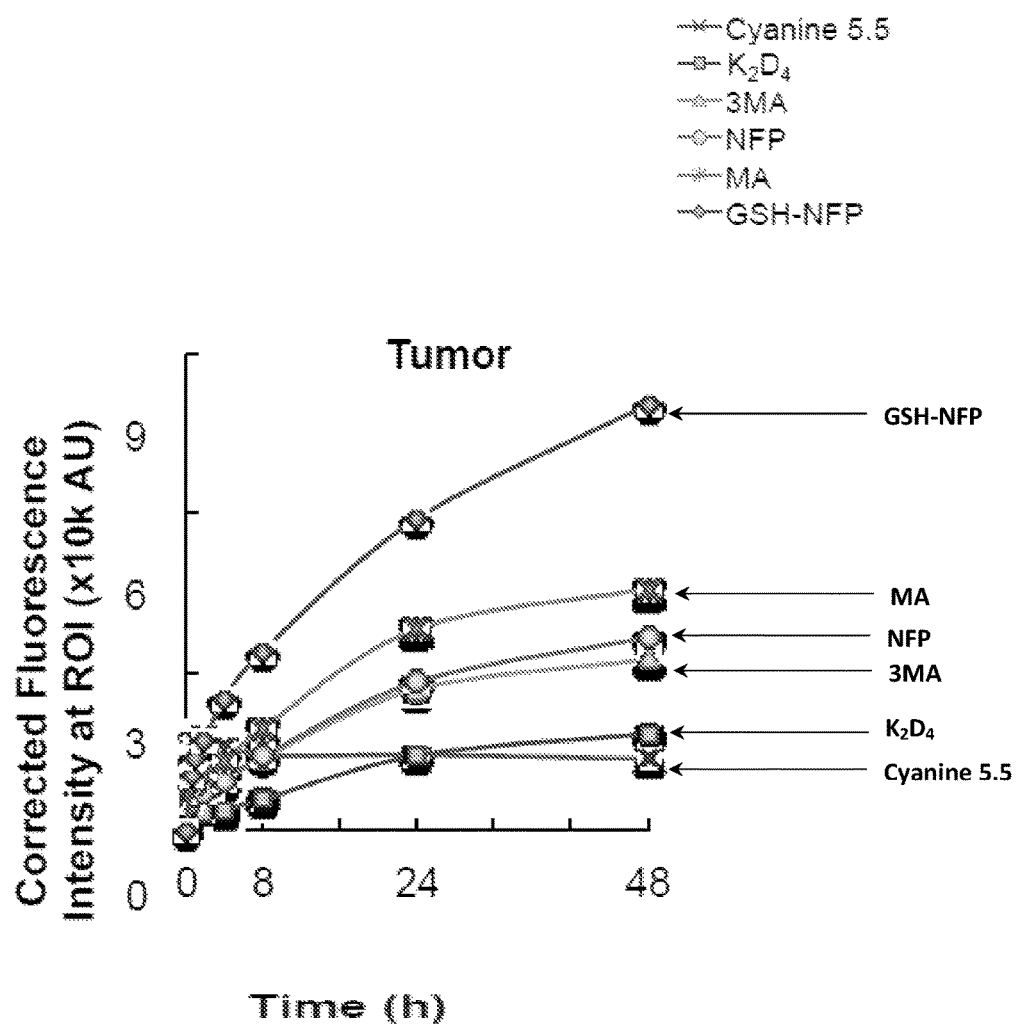
FIG. 12C shows real-time in vivo distribution patterns confirming the tumor-specific uptake and the enhanced tumoral delivery induced by the glutathionylation of the nanofibers. The corrected fluorescence intensity at the region of interest (ROIs) is plotted against time.
Figure 12D:
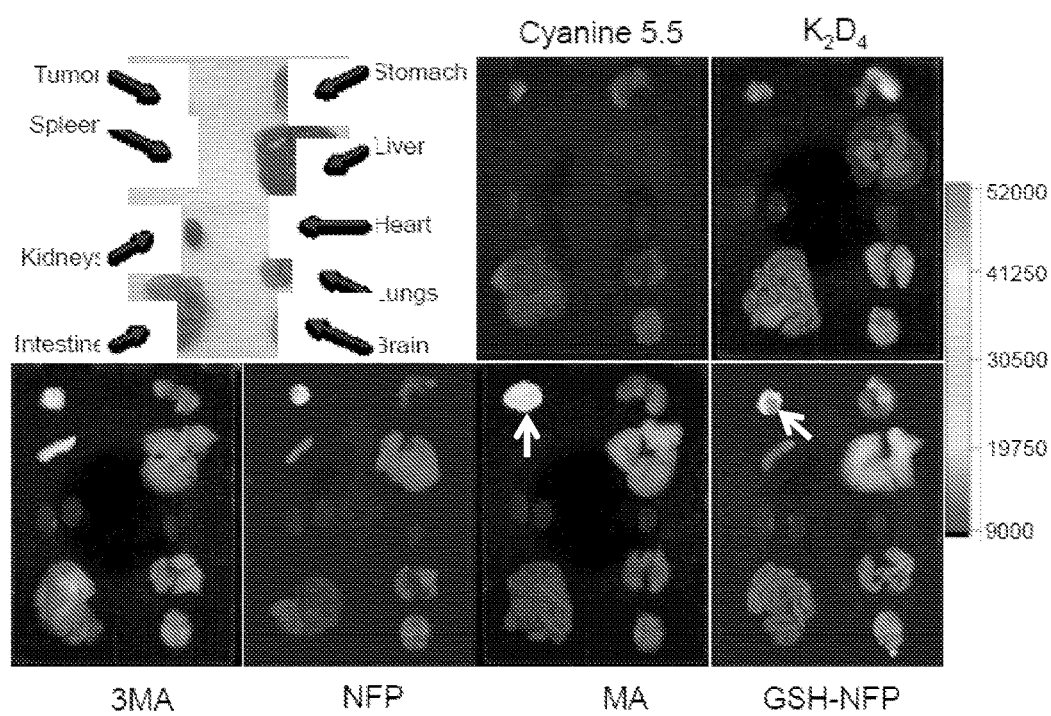
FIG. 12D shows representative ex vivo fluorescence images of the organs isolated from the animals after the in vivo imaging study. White arrows indicate elevated tumoral uptake.
Figure 14:
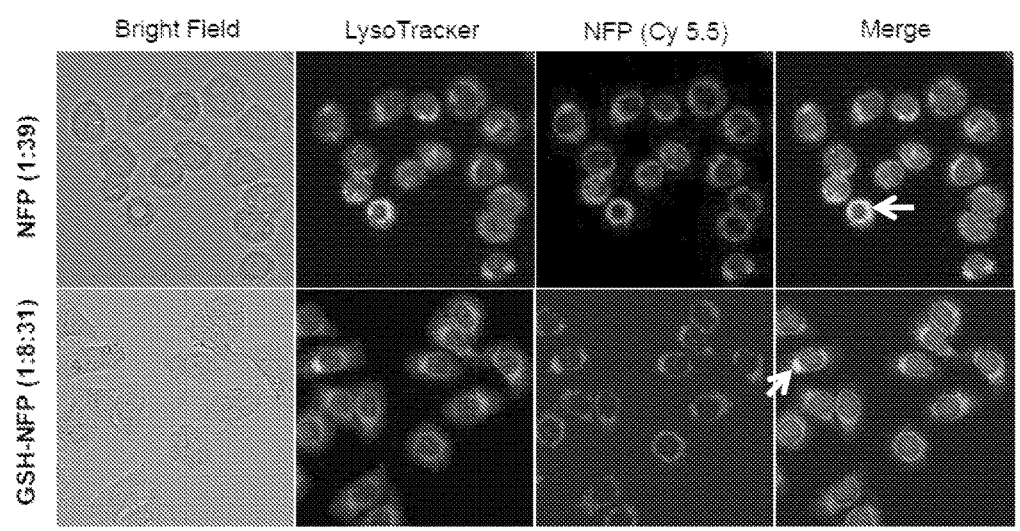
FIG. 14 shows the intracellular distribution of NFP and GSH-NFP in the human triple negative breast cancer cell line MDA-MB-468. Bright field and fluorescence images were acquired 6 h after incubation of the nanofibers (10 µM of peptide content). DAPI (blue) and LysoTracker (green) were used as organelle staining.

The amino acid sequences of the nanofiber precursor analogues NFP, GSH-NFP, K$_2$D$_4$, 3MA and MA are shown in FIG. 12A. Nude mice bearing MDA-MB-468 tumors (n=3/group of animal) were injected in the tail vein with Cy5.5, NFP, GSH-NFP, K$_2$D$_4$, 3MA and MA (0.5 nmol of fluorophore content) and were subjected to periodic fluorescence monitoring. As shown in FIGS. 12B-12D, GSH-NFP shows significantly higher tumoral uptake compared to Cyanine 5.5 and the other tested NFP analogues as early as 8 hours post-injection. Analogues NFP, K$_2$D$_4$, 3MA and MA showed increased tumoral uptake relative to Cy5.5 at 48 hours post-injection. Using the human triple negative breast cancer (TNBC) cell line MDA-MB-468 as the cell model, NFP and GSH-NFP nanofibers were found to predominately accumulate in lysosomes (white arrows) after cellular uptake. FIG. 14.

Figure 13A:
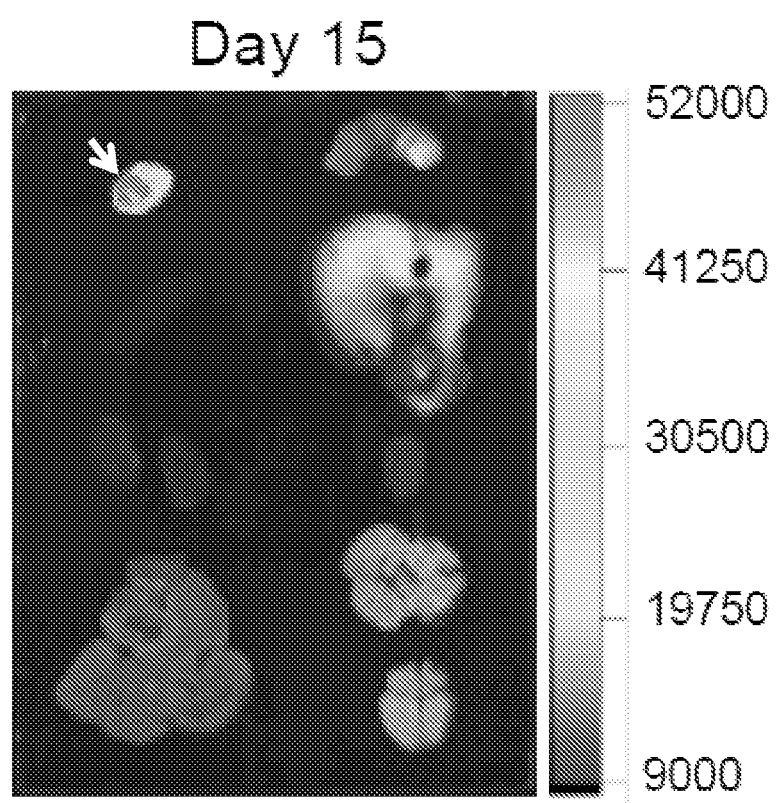
FIG. 13A shows the representative ex vivo fluorescence images of organs isolated from nude mice bearing MDA-MB-468 tumors at day 15 after 3 i.v injections of GSH-NFP (0.5 nmol of fluorophore content).
Figure 13B:
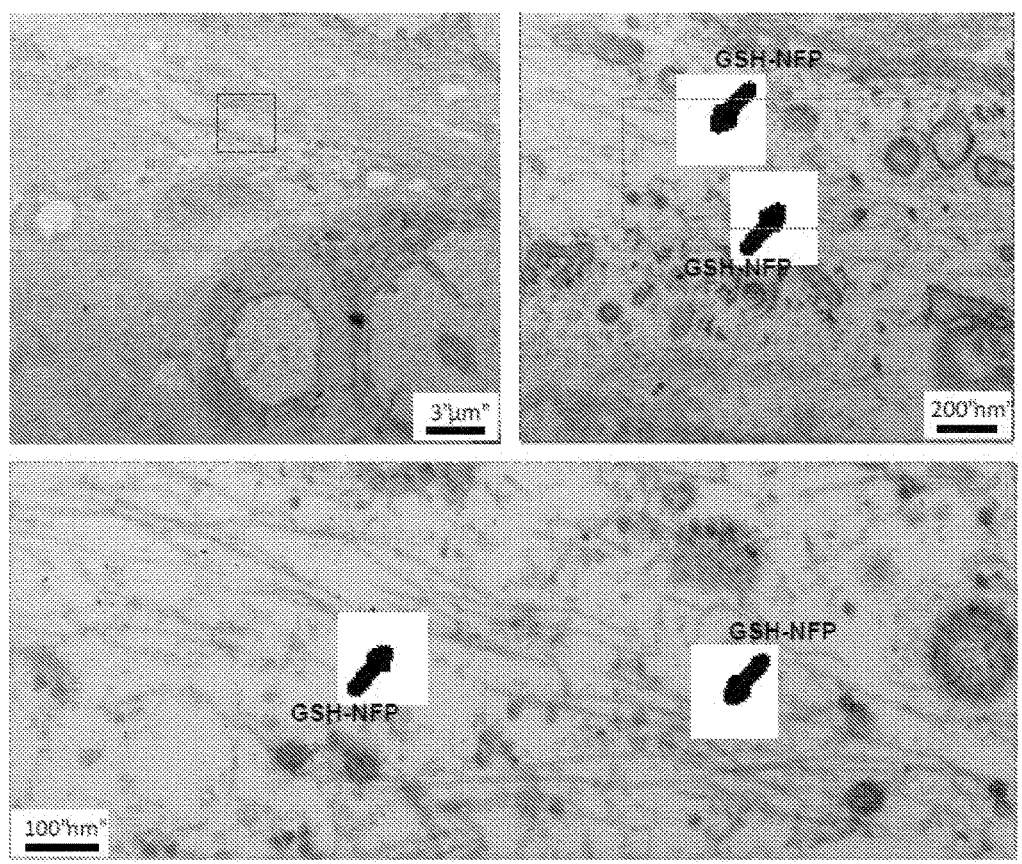
FIG. 13B shows TEM images of GSH-NFP aggregates in tumor excised 48 h after i.v injection of nanofibers. The black arrows point to GSH-NFP large aggregates invading the tumor. Samples were stained with uranyl formate (0.5% v/v) prior TEM imaging.
Figure 16A:
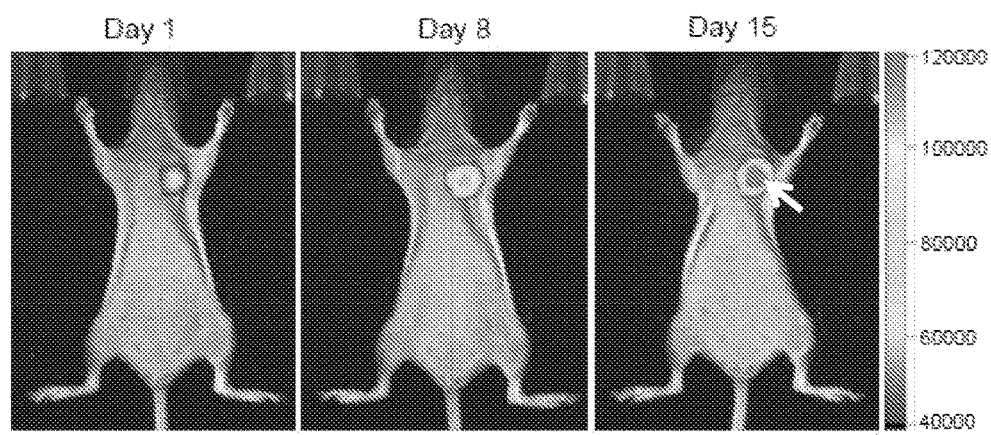
FIG. 16A shows the fluorescence monitoring of nude mice bearing MDA-MB-468 tumors (n=3) after tail vein injection of GSH-NFP homogenized in 400 nm length once a week for 3 weeks (0.5 nmol of fluorophore content). Images were acquired 24 h after each nanofibers administration. The fluorescence intensity increases after each injection suggesting the nanofibers accumulates in the tumor.
Figure 16B:
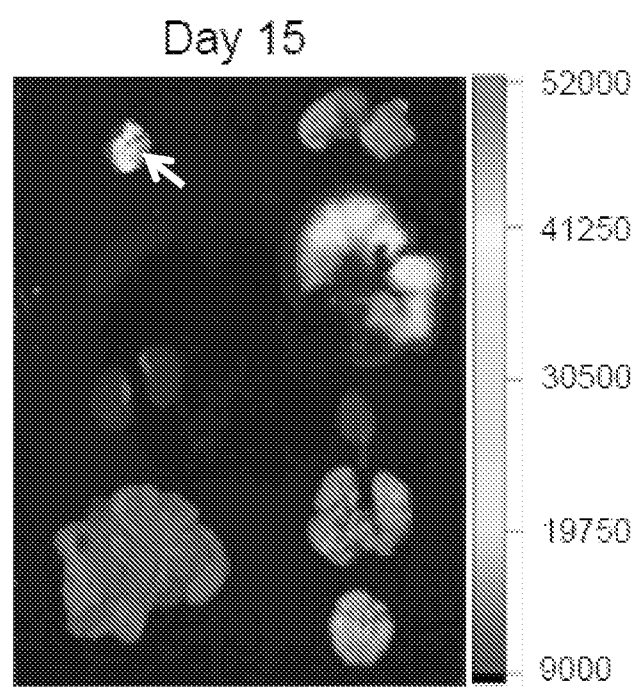
FIG. 16B shows the ex vivo fluorescence image of the organs isolated from the animals at day 15 after 3 i.v. injections of 400 nm GSH-NFP.

Nude mice bearing MDA-MB-468 tumors (n=3) were injected in the tail vein with GSH-NFP once a week for 3 weeks (0.5 nmol of fluorophore content) and were subjected to fluorescence monitoring 24 hours after each peptide-based nanofiber administration. The animals displayed an increase in nanofiber-associated fluorescence after each injection, thus demonstrating accumulation of the nanofibers in tumors. See FIG. 13A (white arrow). Similar results were observed when the animals were injected with GSH-NFP nanofibers having a homogenous length of 400 nm. FIGS. 16A and 16B (white arrows). As shown in FIG. 13B, GSH-NFP aggregates were found in in vivo tumors at 48 hours post-injection.

Figure 15A:
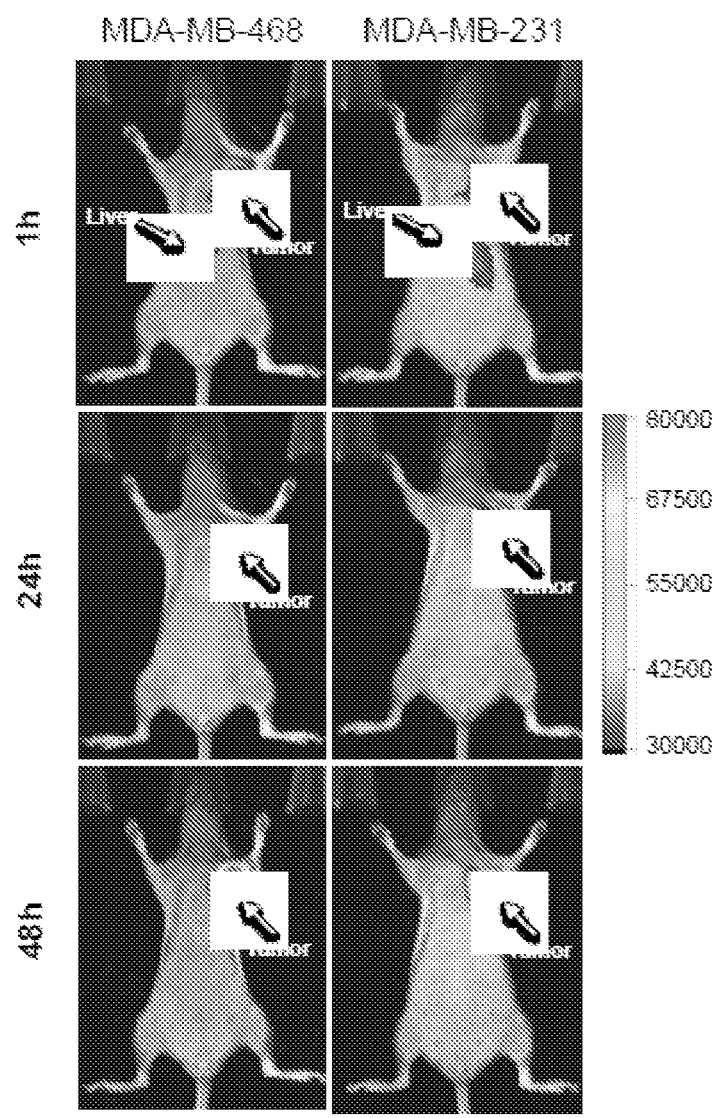
FIG. 15A shows the fluorescence monitoring of nude mice bearing MDA-MB-468 or MDA-MB-231 tumors (n=3/group of animal) after tail vein injection of GSH-NFP (0.5 nmol of fluorophore content). GSH-NFP shows a similar tumoral uptake in the two different classes (basal (MDA-MB-468) and claudin-low (MDA-MB-231)) of human triple negative breast carcinoma.
Figure 15B:
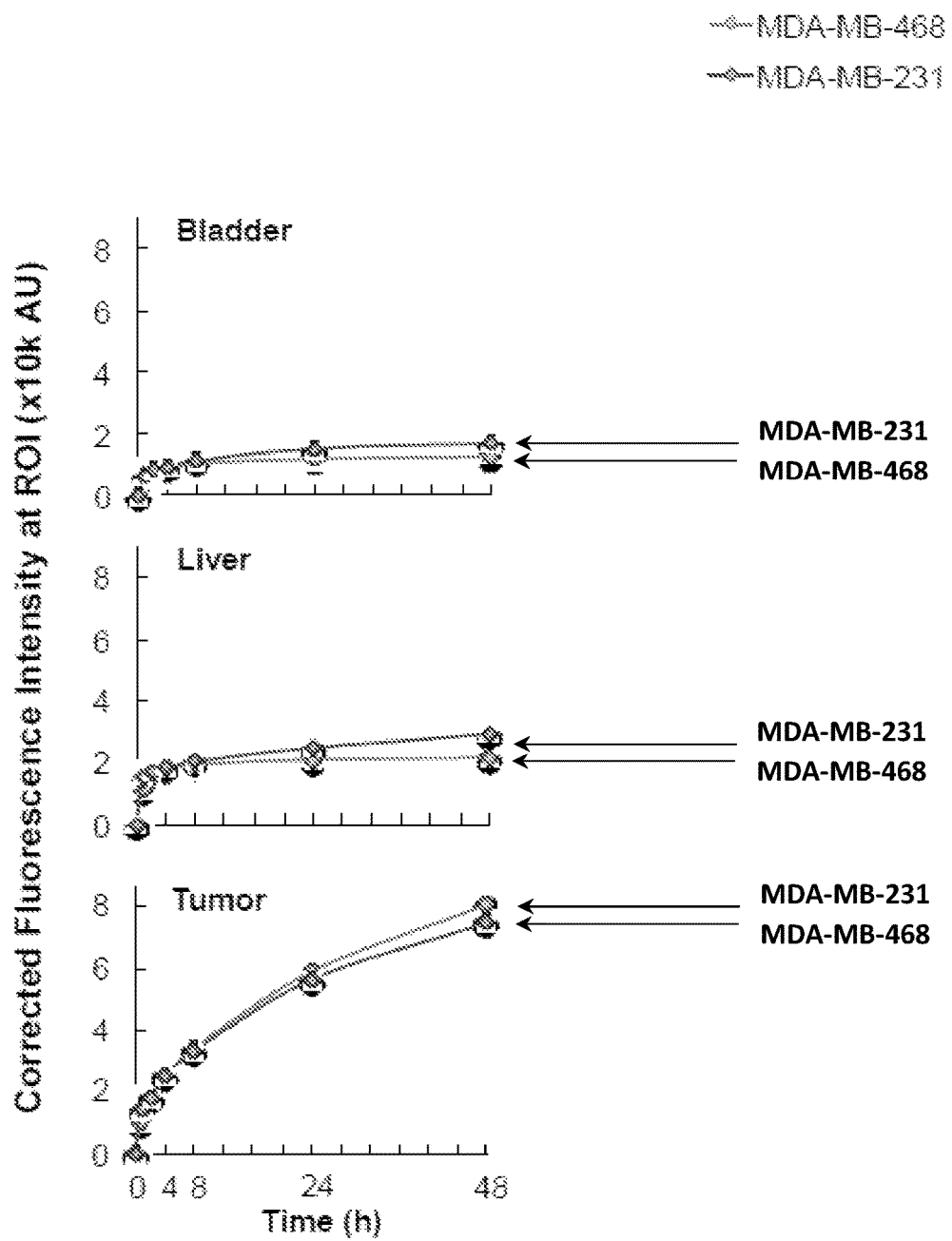
FIG. 15B displays real-time organ distribution. The corrected fluorescence intensity at the region of interest (ROIs) is plotted against time.
Figure 15C:
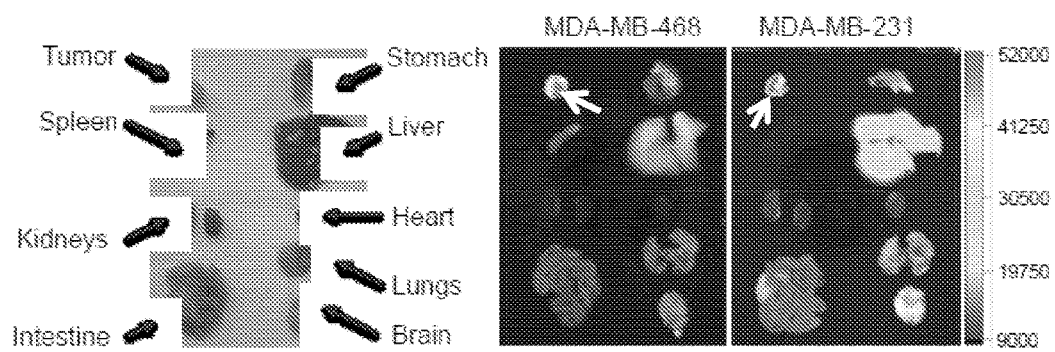
FIG. 15C shows representative ex vivo fluorescence images of the organs isolated from the animals after the in vivo imaging study.

Nude mice bearing MDA-MB-468 or MDA-MB-231 tumors (n=3/group of animals) were injected in the tail vein with GSH-NFP (0.5 nmol of fluorophore content) and were subjected to periodic fluorescence monitoring. As shown in FIGS. 15A and 15B, GSH-NFP nanofibers displayed comparable rates of tumoral uptake in both classes of human triple negative breast carcinoma (basal (MDA-MB-468) and claudin-low (MDA-MB-231)).

These results demonstrate that the peptide-based nanofiber precursor compositions or peptide-based nanofibers of the present technology are useful as carrier complexes. These results demonstrate that the peptide-based nanofiber precursor compositions or peptide-based nanofibers of the present technology are useful in methods for delivering a payload (e.g., a therapeutic or diagnostic agent) to a cancerous cell.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that the present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A peptide-based nanofiber comprising a plurality of peptides, wherein each peptide comprises a methoxypolyethylene glycol (mPEG) polymer, GSH, and a self-assembling domain comprising the sequence KLDLKLDLKLDLK (SEQ ID NO: 1), wherein the self-assembling domain is interspersed between GSH and the mPEG polymer, wherein each amino acid of SEQ ID NO: 1 is an L-amino acid.

2. The peptide nanofiber of claim 1, wherein the mPEG polymer is located at the N-terminus of each peptide.

3. The peptide nanofiber of claim 1, wherein the mPEG polymer has a molecular weight from 1 kDa to 5 kDa.

4. A peptide-based nanofiber comprising a mixture of a first plurality of peptides and a second plurality of peptides,
wherein each peptide of the first plurality of peptides comprises a first methoxypolyethylene glycol (mPEG) polymer, a first fluorophore, and a first self-assembling domain comprising the sequence KLDLKLDLKLDLK (SEQ ID NO: 1), wherein the first self-assembling domain is interspersed between the first fluorophore and the first mPEG polymer, wherein each amino acid of SEQ ID NO: 1 is an L-amino acid; and
wherein each peptide of the second plurality of peptides comprises a second methoxypolyethylene glycol (mPEG) polymer, GSH and a second self-assembling domain comprising the sequence KLDLKLDLKLDLK (SEQ ID NO: 1).

5. The peptide-based nanofiber of claim 4, wherein the molar ratio of the first plurality of peptides to the second plurality of peptides is 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 40:1, or 50:1.

6. A peptide-based nanofiber comprising a mixture of a first plurality of peptides, a second plurality of peptides, and a third plurality of peptides,
wherein each peptide of the first plurality of peptides comprises a first methoxypolyethylene glycol (mPEG) polymer, a first fluorophore, and a first self-assembling domain comprising the sequence KLDLKLDLKLDLK (SEQ ID NO: 1), wherein the first self-assembling domain is interspersed between the first fluorophore and the first mPEG polymer, wherein each amino acid of SEQ ID NO: 1 is an L-amino acid;
wherein each peptide of the second plurality of peptides comprises a second methoxypolyethylene glycol (mPEG) polymer, and a second self-assembling domain comprising the sequence KLDLKLDLKLDLC (SEQ ID NO: 11); and
wherein each peptide of the third plurality of peptides comprises a third methoxypolyethylene glycol (mPEG) polymer, GSH and a third self-assembling domain comprising the sequence KLDLKLDLKLDLK (SEQ ID NO: 1).

7. The peptide-based nanofiber of claim 6, wherein the molar ratio of the third plurality of peptides to the first and second plurality of peptides is 1:49, 2:48, 3:47, 4:46, 5:45, 6:44, 7:43, 8:42, 9:41, or 10:40.

8. The peptide-based nanofiber of claim 6, wherein the molar ratio of the first plurality of peptides to the second plurality of peptides to the third plurality of peptides is 1:31:8, 1:32:7, 1:33:6, 1:34:5, 1:35:4, 1:36:3, 1:37:2, 1:38:1, 1:38.1:0.9, or 1:31.2:0.8.

9. The peptide-based nanofiber of claim 6, wherein the peptide-based nanofiber is surface functionalized with one or more targeting ligands selected from the group consisting of antibodies, polymers, and peptide moieties.

10. The peptide-based nanofiber of claim 9, wherein the peptide moieties are selected from the group consisting of Bombesin (BBN), Somatostatin, Allatostatin 1, Follicle-stimulating hormone analog FSH-33, LyP-1 peptide, Fibroblast growth factor analogs, Hepatocarcinoma targeting peptide, Peptide GFE, Epidermal Growth Factor, cetuximab, RGD tripeptide, CendR peptide, peptide F3, α-MSH peptide, Enterotoxin (STh), cyclic decapeptide CGLIIQKNEC (SEQ ID NO: 6), WIFPWIQL (SEQ ID NO: 7) peptide, CREKA (SEQ ID NO: 8) peptide, IPLVVPL (SEQ ID NO:

9) peptide, KTLLPTP (SEQ ID NO: 10) peptide, and antitumor-antibody-derived peptides.

11. A carrier complex comprising a therapeutic or diagnostic agent conjugated to a peptide-based nanofiber of claim 6.

12. The carrier complex of claim 11, wherein the therapeutic agent is selected from the group consisting of 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, *Bacillus* calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxil, aldoxorubicin, doxifluridine, edrecolomab, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, ibritumomab tiuxetan, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mertansine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, trastuzumab emtansine, tretinoin, trimitrexate, alrubicin, vincristine, vinblastine, vindestine, vinorelbine, vorinostat, and zoledronic acid.

13. The carrier complex of claim 11, wherein the diagnostic agent is a nanoparticle, a radioactive substance, a dye, a fluorescent compound, a contrast agent, a bioluminescent compound, an enzyme, or an enhancing agent.

14. A method for delivering a therapeutic or diagnostic agent to a cancerous cell, the method comprising contacting the cell with the carrier complex of claim 11.

15. A method for delivering a therapeutic or diagnostic agent to a cancerous cell in a subject in need thereof comprising administering to the subject an effective amount of the carrier complex of claim 11.

16. The method of claim 15, wherein the subject is diagnosed with breast cancer, brain cancer, ovarian cancer, or prostate cancer.

17. The method of claim 15, wherein the subject is human.

18. The method of claim 15, wherein the peptide-based nanofiber is administered orally, topically, intranasally, systemically, locally intramuscularly, intravenously, subcutaneously, intracerebroventricularly, intrathecally, intratumorally, transdermally or with iontophoresis.

19. The peptide-based nanofiber of claim 6, wherein the first fluorophore is FITC, TAMRA, or

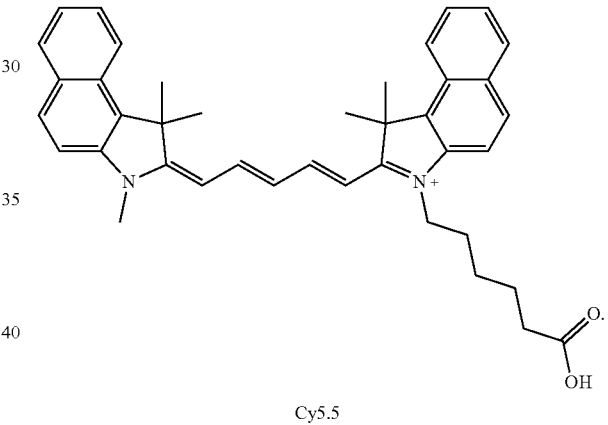

Cy5.5

* * * * *

SEQUENCE LISTING

<160> NUMBER OF SEQ ID NOS: 13

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Leu Asp Leu Lys Leu Asp Leu Lys Leu Asp Leu Lys
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Asp Leu Lys Leu Asp Leu
1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Lys Leu Asp Leu Lys Leu Asp Leu Lys Leu Asp Leu
1               5                   10

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Lys Lys Lys Lys Lys Lys Leu Asp Leu Lys Leu Asp Leu Lys Leu
1               5                   10                  15

Asp Leu Lys

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Lys Lys Lys Lys Lys Lys Leu Asp Leu Lys Leu Asp
1               5                   10

<210> SEQ ID NO 6
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Cys Gly Leu Ile Ile Gln Lys Asn Glu Cys
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Ile Phe Pro Trp Ile Gln Leu
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Arg Glu Lys Ala
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Pro Leu Val Val Pro Leu
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Thr Leu Leu Pro Thr Pro
1               5

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Leu Asp Leu Lys Leu Asp Leu Lys Leu Asp Leu Cys
1               5                   10
```

```
<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Lys Lys Leu Asp Leu Lys Leu Asp Leu Lys Leu Asp Leu Lys Asp
1               5                   10                  15

Asp Asp Asp

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Lys Lys Lys Lys Lys
1               5
```